(12) United States Patent  (10) Patent No.: US 9,198,875 B2
Smith et al.  (45) Date of Patent: Dec. 1, 2015

(54) CONTROLLED DELIVERY OF BIOACTIVE AGENTS FROM DECOMPOSABLE FILMS

(75) Inventors: Renee Chivon Smith, Las Vegas, NV (US); Paula T. Hammond-Cunningham, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 727 days.

(21) Appl. No.: 12/542,267

(22) Filed: Aug. 17, 2009

(65) Prior Publication Data

US 2010/0040674 A1   Feb. 18, 2010

Related U.S. Application Data

(60) Provisional application No. 61/089,560, filed on Aug. 17, 2008.

(51) Int. Cl.
| | |
|---|---|
| *A61K 9/70* | (2006.01) |
| *A61L 27/34* | (2006.01) |
| *A61L 27/54* | (2006.01) |
| *A61L 27/58* | (2006.01) |

(52) U.S. Cl.
CPC ............. *A61K 9/7007* (2013.01); *A61L 27/34* (2013.01); *A61L 27/54* (2013.01); *A61L 27/58* (2013.01); *A61L 2300/402* (2013.01); *A61L 2300/406* (2013.01); *A61L 2300/41* (2013.01); *A61L 2300/416* (2013.01); *A61L 2300/604* (2013.01); *A61L 2300/608* (2013.01); *A61L 2300/802* (2013.01)

(58) Field of Classification Search
None
See application file for complete search history.

(56) References Cited

U.S. PATENT DOCUMENTS

| | | | |
|---|---|---|---|
| 3,266,987 | A | 8/1966 | Crowley et al. |
| 3,710,795 | A | 1/1973 | Higuchi et al. |
| 3,962,414 | A | 6/1976 | Michaels |
| 4,191,811 | A | 3/1980 | Hodgdon |
| 4,250,029 | A | 2/1981 | Kiser et al. |
| 4,460,563 | A | 7/1984 | Calanchi |

(Continued)

FOREIGN PATENT DOCUMENTS

| | | |
|---|---|---|
| DE | 19812083 | 9/1999 |
| DE | 29907804 | 10/1999 |

(Continued)

OTHER PUBLICATIONS

Jessel et al. Multiple and time-scheduled in situ DNA delivery mediated by B-cyclodextrin embedded in a polyelectrolyte multilayer, Jun. 6, 2006, PNAS, vol. 103, No. 23, pp. 8618-8621.*

(Continued)

*Primary Examiner* — Carlos Azpuru
*Assistant Examiner* — Casey Hagopian
(74) *Attorney, Agent, or Firm* — Foley Hoag LLP

(57) ABSTRACT

A decomposable thin film includes a plurality of multilayer units including a first layer having a first charge and a second layer having a second charge, wherein at least a portion of the multilayers includes a polymeric cyclodextrin associated with a bioactive agent, wherein decomposition of the thin film is characterized by sequential removal of at least a portion of the layers having the first charge and degradation of layers having the second charge and by release of the bioactive agent from a corresponding layers; wherein the decomposable thin film including at least one degradable polyelectrolyte layer that is hydrolyzable.

36 Claims, 16 Drawing Sheets

(56) References Cited

U.S. PATENT DOCUMENTS

| | | |
|---|---|---|
| 4,638,045 A | 1/1987 | Kohn |
| 4,794,000 A | 12/1988 | Ecanow |
| 4,806,621 A | 2/1989 | Kohn |
| 4,946,929 A | 8/1990 | D'amore |
| 5,010,167 A | 4/1991 | Ron |
| 5,019,379 A | 5/1991 | Domb |
| 5,114,719 A | 5/1992 | Sabel et al. |
| 5,208,111 A | 5/1993 | Decher et al. |
| 5,364,634 A | 11/1994 | Lew |
| 5,399,665 A | 3/1995 | Barrera |
| 5,462,990 A | 10/1995 | Hubbell et al. |
| 5,512,131 A | 4/1996 | Kumar |
| 5,512,600 A | 4/1996 | Mikos |
| 5,514,378 A | 5/1996 | Mikos |
| 5,518,767 A | 5/1996 | Rubner et al. |
| 5,536,573 A | 7/1996 | Rubner et al. |
| 5,630,941 A | 5/1997 | Burger et al. |
| 5,696,175 A | 12/1997 | Mikos |
| 5,700,559 A | 12/1997 | Sheu et al. |
| 5,714,166 A | 2/1998 | Tomalia et al. |
| 5,716,404 A | 2/1998 | Vacanti |
| 5,716,709 A | 2/1998 | Ferguson et al. |
| 5,736,372 A | 4/1998 | Vacanti |
| 5,770,417 A | 6/1998 | Vacanti |
| 5,797,898 A | 8/1998 | Santini, Jr. et al. |
| 5,804,178 A | 9/1998 | Vacanti |
| 5,807,636 A | 9/1998 | Sheu et al. |
| 5,837,377 A | 11/1998 | Sheu et al. |
| 5,837,752 A | 11/1998 | Shastri |
| 5,858,746 A | 1/1999 | Hubbell et al. |
| 5,902,599 A | 5/1999 | Anseth |
| 5,904,927 A | 5/1999 | Amiji |
| 5,962,520 A | 10/1999 | Smith et al. |
| 6,022,590 A | 2/2000 | Ferguson et al. |
| 6,060,582 A | 5/2000 | Hubbell et al. |
| 6,089,853 A | 7/2000 | Biebuyck et al. |
| 6,095,148 A | 8/2000 | Shastri |
| 6,103,266 A | 8/2000 | Tapolsky et al. |
| 6,114,099 A | 9/2000 | Liu et al. |
| 6,123,681 A | 9/2000 | Brown, III |
| 6,123,727 A | 9/2000 | Vacanti |
| 6,131,211 A | 10/2000 | Hennessey |
| 6,180,239 B1 | 1/2001 | Whitesides et al. |
| 6,235,224 B1 | 5/2001 | Mathiowitz et al. |
| 6,312,727 B1 | 11/2001 | Schacht et al. |
| 6,402,918 B1 | 6/2002 | Schlenoff et al. |
| 6,447,887 B1 | 9/2002 | Claus et al. |
| 6,451,871 B1 | 9/2002 | Winterton et al. |
| 6,479,146 B1 | 11/2002 | Caruso et al. |
| 6,492,096 B1 | 12/2002 | Liu et al. |
| 6,497,729 B1 | 12/2002 | Moussy et al. |
| 6,699,501 B1 | 3/2004 | Neu et al. |
| 6,716,813 B2 | 4/2004 | Lim et al. |
| 6,740,643 B2 * | 5/2004 | Wolff et al. ................. 514/44 R |
| 6,743,521 B2 | 6/2004 | Hubbell et al. |
| 6,833,192 B1 | 12/2004 | Caruso et al. |
| 6,860,980 B2 | 3/2005 | Locascio et al. |
| 6,919,373 B1 | 7/2005 | Lam et al. |
| 6,998,115 B2 | 2/2006 | Langer |
| 7,045,087 B2 | 5/2006 | Kotov |
| 7,045,146 B2 | 5/2006 | Caruso et al. |
| 7,101,575 B2 | 9/2006 | Donath et al. |
| 7,101,947 B2 | 9/2006 | Schlenoff et al. |
| 7,112,361 B2 | 9/2006 | Lynn et al. |
| 7,223,327 B2 | 5/2007 | Schlenoff et al. |
| 7,348,399 B2 | 3/2008 | Haynie |
| 7,364,585 B2 | 4/2008 | Weber |
| 7,365,142 B2 | 4/2008 | Schlenoff et al. |
| 7,427,394 B2 | 9/2008 | Anderson |
| 7,491,263 B2 | 2/2009 | Wang et al. |
| 7,879,575 B2 | 2/2011 | Kricka et al. |
| 8,105,652 B2 | 1/2012 | Wood et al. |
| 2002/0053514 A1 | 5/2002 | Locascio et al. |
| 2002/0131951 A1 | 9/2002 | Langer et al. |
| 2002/0187197 A1 | 12/2002 | Caruso et al. |
| 2003/0059398 A1 | 3/2003 | Ranger et al. |
| 2003/0124368 A1 * | 7/2003 | Lynn et al. ................. 428/483 |
| 2004/0013721 A1 | 1/2004 | Antipov |
| 2004/0020423 A1 | 2/2004 | Lewis et al. |
| 2004/0044100 A1 | 3/2004 | Schlenoff et al. |
| 2004/0052865 A1 | 3/2004 | Gower et al. |
| 2004/0149572 A1 | 8/2004 | Schlenoff et al. |
| 2005/0019404 A1 | 1/2005 | Sung et al. |
| 2005/0152955 A1 | 7/2005 | Akhave et al. |
| 2005/0276841 A1 | 12/2005 | Davis et al. |
| 2006/0127437 A1 | 6/2006 | Kennedy et al. |
| 2006/0198897 A1 | 9/2006 | Pacetti |
| 2006/0216494 A1 | 9/2006 | Furedi-Milhofer et al. |
| 2006/0246112 A1 | 11/2006 | Snyder et al. |
| 2007/0020469 A1 | 1/2007 | Wood et al. |
| 2007/0077276 A1 | 4/2007 | Haynie |
| 2007/0083186 A1 * | 4/2007 | Carter et al. ................. 604/501 |
| 2007/0129792 A1 | 6/2007 | Picart et al. |
| 2007/0141100 A1 | 6/2007 | Sung et al. |
| 2007/0197568 A1 | 8/2007 | Bunn et al. |
| 2008/0228280 A1 | 9/2008 | Cohen et al. |
| 2008/0248108 A1 * | 10/2008 | Krotz et al. ................. 424/463 |
| 2008/0311177 A1 | 12/2008 | Hammond et al. |
| 2009/0053139 A1 | 2/2009 | Shi et al. |
| 2009/0061006 A1 | 3/2009 | Leuschner et al. |
| 2009/0088479 A1 | 4/2009 | Allmendinger et al. |
| 2009/0088679 A1 | 4/2009 | Wood et al. |
| 2009/0155326 A1 | 6/2009 | Mack et al. |
| 2009/0170179 A1 | 7/2009 | Lynn et al. |
| 2009/0214615 A1 | 8/2009 | Zhao |
| 2009/0246142 A1 | 10/2009 | Bhatia et al. |
| 2009/0258045 A1 | 10/2009 | Chuang et al. |
| 2009/0275906 A1 | 11/2009 | Berland et al. |
| 2010/0003499 A1 | 1/2010 | Krogman et al. |
| 2010/0016439 A1 | 1/2010 | Thomes et al. |
| 2010/0189683 A1 | 7/2010 | Holmlund et al. |
| 2011/0038939 A1 | 2/2011 | Lvov et al. |
| 2011/0114244 A1 | 5/2011 | Yoo et al. |
| 2011/0143127 A1 | 6/2011 | Gupta et al. |
| 2011/0301209 A1 | 12/2011 | Zaknoen et al. |
| 2012/0027837 A1 | 2/2012 | DeMuth et al. |
| 2012/0058355 A1 | 3/2012 | Lee et al. |
| 2012/0277719 A1 | 11/2012 | Shukla et al. |
| 2012/0277852 A1 | 11/2012 | Shukla et al. |
| 2013/0190890 A1 | 7/2013 | Shah et al. |
| 2013/0273137 A1 | 10/2013 | Mandell et al. |
| 2014/0039575 A1 | 4/2014 | Bradley et al. |

FOREIGN PATENT DOCUMENTS

| | | |
|---|---|---|
| EP | 0 443 809 | 8/1991 |
| EP | 1 116 516 | 7/2001 |
| EP | 2 162 283 | 9/2010 |
| EP | 2 566 468 | 3/2013 |
| EP | 2 701 908 | 3/2014 |
| GB | 1213803 | 11/1970 |
| GB | 1213805 | 11/1970 |
| WO | WO 95/11748 | 5/1995 |
| WO | WO 95/34595 | 12/1995 |
| WO | WO 96/03147 | 2/1996 |
| WO | WO 98/03573 | 1/1998 |
| WO | WO 98/47948 | 10/1998 |
| WO | WO 99/47253 | 9/1999 |
| WO | WO 00/77281 | 12/2000 |
| WO | WO 01/57118 | 8/2001 |
| WO | WO 01/94441 | 12/2001 |
| WO | WO 02/085500 | 10/2002 |
| WO | WO 03/035716 | 5/2003 |
| WO | WO-2006051227 A1 | 5/2006 |
| WO | WO 2006/086391 | 8/2006 |
| WO | WO 2007/140391 | 12/2007 |
| WO | WO 2007/140402 | 12/2007 |
| WO | WO 2008/157372 | 12/2008 |
| WO | WO 2010/021973 | 2/2010 |
| WO | WO 2010/120531 | 10/2010 |
| WO | WO 2011/140136 | 11/2011 |
| WO | WO 2012/149492 | 11/2012 |
| WO | WO 2012/149494 | 11/2012 |
| WO | WO 2013/110047 | 7/2013 |

(56) References Cited

FOREIGN PATENT DOCUMENTS

| WO | WO 2013/163234 | 10/2013 |
|---|---|---|
| WO | WO 2014/059269 | 4/2014 |
| WO | WO 2014/066862 | 5/2014 |

OTHER PUBLICATIONS

Anderson et al., *Angew. Chem. Int. Ed.* 42:3151, 2003.
Barrera et al. *J. Am. Chem. Soc.* 115:11010-11011, 1993.
Benkirane-Jessel et al., *Advanced Functional Materials.* 14:2, 2004.
Brewster et al. 2007, *Advanced Drug Delivery.* 59: 645-666).
Clark et al., *Supramolecular Science* 4:141, 1997.
Crane et al., *Journal of Chemical Education.* 79:1261, 2002.
Davis et al., *Nature Reviews* (3), 1023-1035, 2004.
Hammond et al., *Macromolecules* 28:7569, 1995.
Jiang et al, *Langmuir,* 16:8501-8509, 2000.
Khopade et al., *Nano Letters.* 2:415, 2002.
Klopman et al., Mini-Reviews in Medicinal Chemistry. 5:127-133, 2005.
Kumar et al., Langmuir 10: 1498, 1994.
Kwon et al., *Macromolecules* 22:3250-3255, 1989.
Langer, *Acc. Chem. Res.* 33:94-101, 2000.
Langer, *J. Control Release* 62:7, 1999.
Lim et al, *J. Am. Chem. Soc.* 123:2460, 2001.
Lim et al. *J. Am. Chem. Soc.* 121:5633-5639, 1999.
Livingstone et al. 2003. *J. Curr. Top. Med. Chem.* 3: 1171-92.
Lynn et al., *J. Am. Chem. Soc.* 122:10761-10768, 2000.
Martin et al. *Supramolecular Chemistry.* 18(8): 627-631, 2006.
Newman et al., *Journal of Natural Products.* 66:1022, 2003.
Nguyen et al., *Chemistry of Materials.* 19:5524, 2007.
Putnam et al. *Macromolecules* 32:3658-3662, 1999.
T. D. Warner et al., *Proceedings of the National Academy of Sciences of the United States of America* 1999, 96, 9966.
Tetko et al., *Comput.-Aided Mol. Des.* 19: 453-463, 2005.
Uhrich et al., *Chem. Rev.* 99:3181, 1999.
Wang et al, *J. Am. Chem. Soc.* 123:9480, 2001.
Wood et al., *Proceedings of the National Academy of Sciences of the United States of America.* 103:10207, 2006.
Zhou et al. *Macromolecules* 23:3399-3406, 1990.
International Search Report for PCT/US2009/054011, 3 pages (Nov. 24, 2010).
Written Opinion for PCT/US2009/054011, 7 pages (Nov. 24, 2010).
Sato, K. et al., Layered Assemblies Composed of Sulfonated Cyclodextrin and Poly(allyamine), Colloid & Polymer Science, 282:287-290 (2004).
Abeloff, M.D. et al., Chapter 95: Cancer of the Breast, in Abeloff's Clinical Oncology, Fourth Edition, pp. 1875-1943, Churchill Livingstone Elsevier (2008).
Albeck, J.G. et al., Modeling a Snap-Action, Variable-Delay Switch Controlling Extrinsic Cell Death, PLoS Biology, 6(12):2831-2852 (2008).
Anderson, "Human Gene Therapy" *Nature,* 392: 25-30 (1996).
Anderson, et al., "Biodegradation and Biocompatibility ofPLA and PLGA Microspheres" *Adv. Drug Delivery Rev.* 28: 5-24, 1997.
Ando, et al., "PLGA Micospheres Containing Plasmid DNA: Preservation of Supercoiled DNA via Cryopreparation and Carbohydrate Stabilization" *J. Pharm. Sci.* 88: 126-130, 1999.
Antipov, et al., "Sustained Release Properties of Polyelectrolyte Multilayer Capsules" J. Phys. Chem., 105:2281-2284 (2001).
Balko, J.M. et al., Gene expression patterns that predict sensitivity to epidermal growth factor receptor tyrosine kinase inhibitors in lung cancer cell lines and human lung tumors, BMC Genomics, 7:289-302 (2006).
Bass, Brenda L., "RNA Interference The Short Answer", *Nature* 411, 428-429, 2001.
Behr, "Synthetic Gene-Transfer Vectors" *Ace. Chern. Res.* 26: 274-278, 1993.
Behr, "The Proton Sponge: a Trick to Enter Cells the Viruses Did Not Expoit" *Chimia,* 51: 34- 36, 1997.

Bott "Applications of "Wired" Enzyme Electrodes," Current Separations, 21(1):3-6 (2004).
Boussif, et al., "A Versatile Vector for Gene and Oligonucleotide Transfer into Cells in Culture and In Vivo: Polyethylenimine" *Proc. Nat/. Acad. Sci, USA,* 92: 7297-7301, 1995.
Brazeau, et al., "In Vitro Myotoxicity of Selected Cationic Macromolecules Used in Non-1tb1 Gene Delivery"*Pharm. Res.* 15: 680-684, 1998.
Buser et al., "The Crystal Structure of Prussian Blue: $Fe_4[Fe(CN)_5]_3XH_2O$," Inorganic D Chemistry, 16(11 ):2704-271 0 (1977).
Calvo et al. "Donnan Permselectivity in Layer-by-Layer Self-Assembled Redox Polyelectrolyte thin film", J. Am. Soc. 124: 8490-8497(2002).
Carey, L.A. et al., "EGFR inhibition with cetuximab added to carboplatin in metastatic triple-negative (basal-like) breast cancer," *Supplement to Journal of Clinical Oncology, ASCO Annual Meeting Proceedings, TBCRC 001: Clinical Science Symposium,* 43S (2009).
Carpenter et al., "A Single-Film Electrochromic Device," J. Electrochem. Soc., 137(8):2464-2467 (1990).
Carpenter, A. E. et al., CellProfiler: image analysis software for identifying and quantifying cell phenotypes, Genome Bioloqy, 7(10):R100-R100.11 (2006).
Castleberry, S., et al., "Nanolayered siRNA Dressing for Sustained Localized Knockdown," *ACS Nano,* 7(6): 5251-5261 (2013).
Castleberry, S., et al., "Surface Mediated Delivery of siRNA from Layer-By-Layer Assembled Polyelectrolyte Films for the Acceleration of Wound Healing," Abstracts of Papers, 244th National Mtg & Exposition, Aug. 19-23, 2012.
Chen, "Preparation, characterization, and electrocatalytic oxidation properties of iron, cobalt, nickel, and indium hexacyanoferrate," Journal of Electroanalytical Chemistry, 521:29-52 (2002).
Choksakulnimitr et al., "In Vitro Cytotoxicity of Macromolecules in Different Cell Culture Systems" *Controlled Release,* 34: 233-241 (1995).
Chou, T-C. et al., Quantitative Analysis of Dose-Effect Relationshiios: The Combined Effects of Multiple Drugs or Enzyme Inhibitors, Advances in Enzyme Regulation, 22:27-55 (1984).
Christensen et al., "Heparin coating of the stent graft—effects on platelets, coagulation and complement activation," Biomaterials, 22:349-355 (2001).
Corkery, B. et al., Epidermal growth factor receptor as a potential therapeutic target in triple-negative breast cancer, Annals of Oncology, 20:862-867 (2009).
Cotten, et al., "Receptor-Mediated Transport of DNA into Eukaryotic Cells" *Methods Enzym.* 217:618, 1993.
Crystal, "Transfer of Genes to Humans: Early Lessons and Obstacles to Success" *Science,* 270: 404-410 (1995).
Danusso, et al., "Synthesis of Tertiary Amine Polymers" *Polymer,* 11:88-113 (1970).
Decher et al., "Buildup of Ultrathin Multilayer Films by a Self-Assembly Process, 1 Consecutive Adsorption of Anionic and Cationic Bipolar Amphiphiles on Charged Surfaces," Makromol. Chem., Macro mol. Symp., 46:321-327 (1991).
Decher et al., "Buildup of Ultrathin Multilayer Films by a Self-Assembly Process: II.Consecutive Adsorption of Anionic and Cationic Bipolar Amphiphiles and Polyelectrolytes on Charged Surfaces," Ber. Bunsenges. Phys. Chem., 95(11 ):1430-1434 (1991).
Decher et al., "Layer-by-layer assembled multicomposite films," Curr. Opinion Coli. & Interf. Sci., 3:32-39 (1998).
Decher et al., "New nanocomposite films for biosensors: layer-by-layer adsorbed films of polyelectrolytes, proteins or DNA," *Biosensors & Bioelectronics,* 9:677-684 (1994).
Decher, "Fuzzy Nanoassemblies: Toward Layered Polymeric Multicomposites" *Science,* 277: 1232-1237 (1997).
Delongchamp "High-Contrast Electrochromism from Layer-By-Layer Polymer Films," Chem. Mater, 15: 1575-1586 (2003).
Delongchamp et al., "Fast Ion Conduction in Layer-By-Layer Polymer Films," Chern. Mater., 15:1165-1173 (2003).
Delongchamp et al., "High-Contrast Electrochromism and Controllable Dissolution of Assembled Prussian Blue/Polymer Nanocomposites," Adv. Funct. Mater., 14(3):224-231 (2004).

(56) References Cited

OTHER PUBLICATIONS

Demeneix, et al., "The Proton Sponge: A Trick the Viruses Did Not Exploit," *American Chemical Society*,146-151 (1996).
Dent, R. et al., "Triple-Negative Breast Cancer: Clinical Features and Patterns of Recurrence," *Clinical Cancer Research*, 13: 4429-4434 (2007).
Deshmukh, et al., "Liposome and Polylysine Mediated Gene Transfer" *New J. Chem.* 21:113-124 (1997).
Diaz, R. et al., "Antitumor and anti angiogenic effect of the dual EGFR and HER-2 tyrosine kinase inhibitor lapatinib in a lung cancer model," *BMC Cancer*, 10:188 (2010).
Dowben, R.M., "General Physiology: A Molecular Approach," Division of Biological and Medical Sciences, pp. 142-143, Harper & Row Publishers (1969).
Dubas, et al., "Multiple Membranes from 'True' Polyelectrolyte Multilayers", *J. Am. Chem. Soc.*, 123:5368-5369 (2001).
Dubas, et al., Polyelectrolyte Multilayers Containing a Weak Polyacid: Construction and Deconstruction, *Macromolecules*, 34: 3736-3740 (2001).
Duek et al., "A Solid-State Electrochromic Device Based on Polyaniline, Prussian Blue and an Elastomeric Electrolyte," Advanced Materials, 5(9):650-652 (1993).
Ekins, S. et al., Pathway Mapping Tools for Analysis of High Content Data, Methods in Molecular Biology, 356:319-350 (2007).
Elbert et al., "Self-assembly and steric stabilization at heterogeneous, biological surfaces using absorbing block copolymers" Chemistry & Biology 5(3): 177-183 (1998).
Ellis et al., "Eietrochromism in the Mixed-Valence Hexacyanides. 1. Voltammetric and Spectral Studies of the Oxidation and Reduction of Thin Films of Prussian Blue," J. Phys. Chem., 85:1225-1231 (1981).
Ferruti, e.t al., "Synthesis, Characterisation and Anti tumour Activity of Platinum (II) Complexes ofNovel Functionalised Poly (Arnido Amine)s" *Macromol. Chem. Phys.* 200:1644-1654, 1999.
Ferruti, et al., "Amphoteric Linear Poly(amido-amine)s as Endosomolytic Polymers: Correlation between Physicochemical and Biological Properties", *Macromolecules*, 2000.
Ferruti, et al., "Linear Amino Polymers: Synthesis, Protonation and Complex Formation" *Advances in Polymer Science*, 58: 55-92, 1984.
Ferruti, et al., "Recent Results on Functional Polymers and Macromonomers offuterest as Biomaterials or for Biomaterial Modifcation" *Biomaterials*, 15: 1235-1241, 1994.
Ferruti, et al., "Synthesis, Physico-Chemical Properties and Biomedical Applications of Poly(amino-amine)s" Polymer, 26: 1336 (1985).
Fire, et al., "Potent and Specific Genetic Interference by Double-Stranded RNA in Caenorhabditis Elegans" *Nature*, 391: 806-811 (1998).
Fitzgerald, J.B., et al., Systems biology and combination therapy in the quest for clinical efficacy, Nature Chemical Biology, 2(9):458-466 (2006).
Freiberg, et al., "Polymer microspheres for controlled drug release," *Int. J. Pharm.* 282:1-18 (2004).
Friedman, "Human Gene Therapy—An Immature Genie, But Certainly out of the Bottle" *Nature Med*, 2: 144-147 (1996).
Flessner, R.M., et al., "Degradable Polyelectrolyte Multilayers That Promote the Release of siRNA," 27(12): 7868-7876 (2011).
Gao, et al., "Layer-By-Layer Electrodeposition of Redox Polymers and Enzymes on Screenprinted Carbon Electrodes for the Preparation of Reagentless Biosensors," *Chem Comm*, (2003).
Gaudet, S., et al., "A Compendium of Signals and Responses Triggered by Pro-death and Prosurvival Cytokines," *Molecular & Cellular Proteomics*, 4:1569-1590 (2005).
Gerasimov, et al., "Cytosolic Drug Delivery Using pH- and Light-Sensitive Liposomes" *Adv. Drug Delivery Rev.* 38: 317-338 (1999).
Gonzalez, et al., "New Class of Polymers for the Delivery of Macromolecular Therapeutics" *Bioconjugate Chem.* 10: 1068-1074 (1999).
Grayson, et al., "Electronic MEMS for triggered drug delivery," *Advanced Drug Delivery Reviews*, 56:173-184 (2004).

Guo, P., "Rolling Circle Transcription of Tandem siRNA to Generate Spherulitic RNA Nanoparticles for Cell Entry," Molecular Therapy, Nucleic Acids, 1:3162-2531 (2012).
Grabow, W. W., et al., "siRNA delivery: Loaded-up Microsponges," Nature Materials, 11(4): 268-269 (2012).
Habib, et al., "A tungsten-trioxide/prussian blue complementary eletrochromic cell with a polymer electrolyte," *Journal of Applied Electrochemistry*, 21:203-207 (1991).
Habib, et al., "Effect of Temperature on a Complementary W03-Prussian Blue Electrochromic System," *J. Electrochem. Soc.*, 139(8):2155-2157 (1992).
Haensler, et al., "Polyamidoamine Cascade Polymers Mediate Efficient Transfection of Cells in Culture" *Bioconjugate Chem.*, 4:372-379 (1993).
Hammond, "Form and Function in Multilayer Assembly: New Applications at the Nanoscale," *Adv. Mater.*, 16:1271-1293 (2004).
Hanahan, D. et al., "The Hallmarks of Cancer," *Cell*, 100: 57-70 (2000).
Hanes, et al., "New Advances in Microsphere-Based Single-Dose Vaccines" *Adv. Drug Delivery Rev.* 28:97-119 (1997).
Hansen, et al., "Re-Examination and Further Development of a Precise and Rapid Dye Method for Measuring Cell Growth/Cell Kill" *Immunol. Methods*, 119:203-210, 1989.
Harper, J.W., et al., The DNA Damage Response: Ten Years After, Molecular Cell, 28(5):739-745 (2007).
Hehrlein, et al., "Drug-eluting stent: the "magic bullet" for prevention of restenosis?" Basic Res Cardiel, 97:417-423 (2002).
Helfrich, B.A., et al., Antitumor Activity of the Epidermal Growth Factor Receptor (EGFR) Tyrosine Kinase Inhibitor Gefitinib (ZD1839, lressa) in Non-Small Cell Lung Cancer Cell Lines Correlates with Gene Copy Number and EGFR Mutations but not EGFR Protein Levels, Clinical Cancer Research, 12:7117-7125 (2006).
Heller "Redox hydrogel-based electrochemical biosensore," Biosensors, Second Edition, pp. 1-18 (2004).
Hill, et al., "In Vitro Cytotoxicity of Poly(amidoamine)s: Relevance to DNA Delivery" Biochim. Biophys. Acta, 1427: 161q 74 (1999).
Hope, et al., Cationic Lipids, Phosphatidylethanolamine and the Intracellular Delivery of Polymeric, Nucleic Acid-Based Drugs (Review), *Molecular Membrane Technology*, 15: 1-14 (1998).
Itaya, et al., "Prussian-blue-modified electrodes: An application for a stable eletrochromic display device," *J. Appl. Phys.*, 53:804-805 (1982).
Janes, K.A., et al., A Systems Model of Signaling Identifies a Molecular Basis Set for Cytokine-lnduced Apoptosis, *Science*, 310:1646-1653 (2005).
Janes, K.A., et al., Cytokine-lnduced Signaling Networks Prioritize Dynamic Range over Signal Strength, *Cell*, 135:343-354 (2008).
Jelle, et al., "Transmission Spectra of an Electrochromic Window Consisting of Polyaniline, Prussian Blue and Tungsten Oxide," Electrochimica Acta, 38(11 ):1497-1500 (1993).
Kabanov, et al., "DNA Complexes with Polycations for the Delivery of Genetic Material inot Cells" *Bioconjugate Chem*. 6:7-20 (1995).
Kang, N. et al., Inhibition of EGFR signaling augments oridonin-induced apoptosis in human laryngeal cancer cells via enhancing oxidative stress conicident with activiation of both the intrinsic and extrinsic apoptotic pathways, Cancer Letters, 294:147-158 (2010).
Карги на, О.В. Caмopacш Еп л я ioИ и ЕСя ВО Д ОРАСТВОРИ МВIE И ОНОГ ЕННbIЕ П ОЛ И МЕРbI; English Summary: Kargina, et al., "Self-Splitted Water-Soluble lonogenic Polymers" *Vysokomol. Soedin. Seriya A*, 28: 1139-1144 (1986). (English Abstract).
Kim, R., Recent Advances in Understanding the Cell Death Pathways Activated by Anticancer Therapy, Cancer, 1 03(8):1551-1560 (2005).
Kukowska-Latallo, et al., "Efficient Transfer of Genetic Material into Manunalian Cells Using Starburst Polyamidoamine Dendrimers" *Proc. Nat/. Acad. Sci. USA*, 93: 4897-4902, (1996).
Lavan, et al., "Small-scale systems for in vivo drug delivery," *Nature Biotechnology*, 21(10):1184-1191 (2003).
Lee, J.B., et al., "Self-assembled RNA interference microsponges for efficient siRNA delivery," Nature Materials, 11(4): 316-322 (2012).
Lichter, A.S., et al., "Recent Advances in Radiation Oncology," *New England Journal of Medicine*, 332(6):371-379 (1995).

(56) References Cited

OTHER PUBLICATIONS

Lim, et al., "Development of a Safe Gene Delivery System Using Biodegradable Polymer, Poly [a-(4-Aminobutyl-L-Glycolic Acid]" *Journ. Chem. Soc.* 122: 6524-6525 (2000).

Linhardt, et al., "Free-Radical Synthesis of Poly(2-Ethylacrylic Acid) Fractions of Low Polydispersity: Effects of Molecular Weight and Polydispersity on the pH-Dependent Conformational Transition in Aqueous Solution" *Macromolecules*. 32: 4457-4459 (1999).

Linhardt,• et al., "pH-Induced Fusion and Lysis of Phosphatidylcholine Vesicles by Hydrophobic Polyelectrolyte Poly(2-ethylacrylic Acid)" *Langmuir*, 16: 122-127 (2000).

Lopez, J.P. et al., Gefitinib Inhibition of Drug Resistance to Doxorubicin by Inactivating ABCG2 in Thyroid Cancer Cell Lines, Archives of Otolaryngology- Head & Neck Surgery, 133(10):1022-1027 (2007).

Luo, et al., "Synthetic DNA Delivery Systems" *Nat. Biotechnol.* 18: 33-37, 2000.

Lynn et al., "pH-Responsive Polymer Microspheres: Rapid Release of Encapsulated Material Within the Range of Intracellular pH" Angewandte Chemie International Edition 2001, 40, 1707-1710.

Lynn, et al., "Accelerated Discovery of Synthetic Transfection Vectors: Parallel Synthesis and Screening of a Degradable Polymer Library" Journal of the American Chemical Society 2001, 123, 8155-8156.

Lynn, et al., Construction of Degradable Thin Films via Layber-by-Layer Deposition of Polyelectrolytes: Fabrication, Characterization, and Application to Controlled Release, MIT Proposal 2001.

Macbeath, G., Protein microarrays and proteomics, Nature Genetics Supplement, 32:526-532 (2002).

Macdonald et al., "Tissue Integration of Growth Factor-Eluting Layer-by-Layer Polyelectrolyte Multilayer Coated Implants," *Biomaterials*, 32(5): 1446-1453 (2010).

Mathiowitz, et al., "Polyanhydride Microspheres as Drug Carriers I. Hot-Melt Microencapsulation" *J. Controlled Release*, 5:13-22 (1987).

Mathiowitz, et al., "Polyanhydride Microspheres as Drug Carriers. II. Microencapsulation" *J. Appl. Polymer Sci.*, 35: 755-774 (1988).

Michel, et al., "Printing meets lithography: Soft approaches to high-resolution patterning" IBM Journal of Research and Development, 45(5): 697-719 (2001).

Milano, G. et al., EGFR-targeting drugs in combination with cytotoxic agents: from bench to bedside, a contrasted reality, British Journal of Cancer, 99:1-5 (2008).

Miller, "Cationic Liposomes for Gene Therapy" *Angew. Chern. Int. Ed.* 37: 1769-1785, 1998.

Mizushima, N. et al., Methods in Mammalian Autophagy Research, Cell, 140:313-326 (2010).

Moor, A., et al., "Proteolytic Activity in Wound Fluids and Tissues Derived from Chronic Venous Leg Ulcers," *Wound Repair and Regeneration*, 17(6): 1067-1927 (2009).

Montesano, R. et al., Test for Malignant Transformation of Rat Liver Cells in Culture: Cytology, Growth in Soft Agar, and Production of Plasminogen Activator, *Journal of the National Cancer Institute*, 59(6):1651-1658 (1977).

Morgillo, F. et al., Antitumor activity of bortezomib in human cancer cells with acquired resistance to anti-epidermal growth factor receptor tyrosine kinase inhibitors, Lung Cancer, 71 :283-290 (2011 ).

Moriguchi et al., "Synthesis of Ultrathin Films of Prussian Blue by Successive Ion Adsorption Technique," Chemistry Letters, 31 (3):310-311 (2002).

Mulligan, "The Basic Science of Gene Therapy" *Science*, 260: 926-932 (1993).

Murphy, et al., "A Combinatorial Approach to the Delivery of Efficient Cationic Peptoid Reagents for Gene Delivery", *Proc. Natl. Acad. Sci. USA*, 95: 1517-1522 (1998).

Neve, R.M. et al., A collection of breast cancer cell lines or the study of functionally distinct cancer subtypes, Cancer Cell, 10:515-527 (2006).

O'Donnell, et al., "Preparation of Microspheres by the Solvent Evaporation Technique" *Adv. Drug Delivery Rev.*, 28:25-42, 1997.

Okada, "One-and Three- Month Release Injectable Microspheres of the LH-RH Superagonist Leuprorelin Acetate" *Adv. Drug Delivery Rev.* 28: 43-70, 1997.

Olivia et al., "Antiproliferative Drug-Eluting Stents: Systematic Review of the Benefits and Estimate of Economic Impact," Rev Esp Cardiel, 57(7):617-628 (2004).

Pasco et al., "Characterization of a thermophilic L-glutamate dehydrogenase biosenor for amperometric determination of L-glutamate by flow injection analysis," Biosensors & Bioelectronics, 14:171-178 (1999).

Pawson, T. et al., Network medicine., FEBS Letters, 582:1266-1270 (2008).

Peerce et al., "Polymer Films on Electrodes, Part Ill. Digital Simulation Model for Cyclic Voltammetry of Electroactive Polymer Film and Electrochemistry of Poly(vinylferrocene) on Platinum," J. Electroanal. Chern, 114:89-115 (1980).

Perou, C.M. et al., Molecular portraits of human breast tumours, Nature, 406:747-752 (2000).

Pfeifer et al., "Formulation and surface modification of poly( ester-anhydride) micro- and nanoshperes," Biomaterials, 26:117-124 (2005).

Picart et al., "Molecular basis for the explanation of the expotential growth of polyelectrolyte multilayers" PNAS 99(20):12531-12535 (2002).

Poerner et al., "Drug-coated stents," Minimally Invasive Therapy & Allied Technologies 11(4):185-192 (2002).

Qiu, et al., "Studies on the Drug Release Properties of Polysaccharide Multi layers Encapsulated Ibuprofen Microparticles" Langmuir 17: 5375-5380 (2001).

Rajan et al., "Eiectrochromism in the Mixed-Valence Hexacyanides. 2. Kinetics of the Reduction of Ruthenium Purple and Prussian Blue," J. Phys. Chern., 86:4361-4368 (1982).

Rao, et al., "Poly (Butaneodiol Spermate): A Hydrolytically Labile Polyester-Based Nitric Oxide Carrier" J. Bioactive and Compatible Polymers 14: 54-63, 1999.

Razzacki et al., "Integrated microsystems for controlled drug delivery," Advanced Drug Delivery Reviews, 56:185-198 (2004).

Roberts, et al., "Preliminary Biological Evaluation of Polyamidoamine (P AMAM) Starburst TM Dendrimers" *J. Biomed. Mater. Res.* 30: 53-65, 1996.

Robin et al., "The Color and Electronic Configurations of Prussian Blue," Electronic Configurations of Prussian Blue, 1( 2):337-342 (1962).

Rusnak, D.W. et al., Assessment of epidermal growth factor receptor (EGFR, ErbB1) and HER2 (ErbB2) protein expression levels and response to lapatinib (Tykerb®, GW572016) in an expanded panel of human normal and tumour cell lines, Cell Proliferation, 40: 580-594 (2007).

Sachs, K. et al., Casual Protein-Signaling Networks Derived from Multiparameter Single-Cell Data, Science, 308:523-529 (2005).

Sanford, "The Biolistic Process" Trends Biotechnol. 6:288-302, 1988.

Santini et al., "Microchips as Controlled Drug-Delivery Devices," Angew. Chern. Int. Ed., 39:2396-2407 (2000).

Santini et al., "Microchips for drug delivery," Abstracts of Papers of the American Chemical Society, 219(174):U34-U34 (2000).

Sapi, E. et al., Ets-2 Transdominant Mutant Abolishes Anchorage-independent Growth and Macrophage Colony-stimulating Factor-stimulated Invasion by BT20 Breast Carcinoma Cells, Cancer Research, 58:1027-1033 (1998).

Schaffer, et al., "Vector Unpacking as a Potential Banier for Receptor-Mediated Polyplex Gene Delivery" *Biotechnol. Bioeng*.61: 598-606,2000.

Schechter, A.L. et al., The *neu* oncogene: an erb-8-related gene encoding a 185,000-Mr tumour antiQen, Nature, 312:513-516 (1984).

Schuler "Decomposable Hollow Biopolymer-Based Capsules" Biomacromolecules, vol. 2, 2001 921-26.

Schweikl, et al., "Triethylene Glycol Dimethacrylate Induces Large Deletions in the Hprt Gene of V79 Cells" *Mutat. Res.* 438: 71-78 (1999).

(56) References Cited

OTHER PUBLICATIONS

Sengupta, S. et al., Temporal targeting of tumor cells and neovasculature with a nanoscale delivery system, Nature, 436:568-572 (2005).
Sevecka, M. et al., State-based discovery: a multidimensional screen for small-molecule modulators of EGF signaling, Nature Methods, 3(1 0):825-831 (2006).
Seyhan, A. A., et al., "RNA interference from Multimeric shRNSs generated by rolling circle transcripotion," Oligonucleotides, 16(4): 353-363 (2006).
Shiratori et al., "pH-Dependent Thickness Behavior of Sequentially Adsorbed Layers of Weak Polyelectrolytes," Macormolecules, 33:4213-4219 (2000).
Shkula et al., "Tunable Vancomycin Releasing Surfaces for Biomedical Applications", Small Nano Mirco, 21(6): 2392-2404 (2010).
Singh, et al., "Cationic Microparticles: A Potent Delivery System for DNA Vaccines" Proc. Nat/. Acad. Sci. USA, 97: 811-816 (2000).
Slamon, D.J. et al., Human Breast Cancer: Correlation of Relapse and Survival with Amplification of the HER-2/neu Oncogene, Science, 235:177-182 ( 1987).
Smith et al., "Layer-by-Layer Platform Technology for Small-Molecule Delivery", Anqew. Chem.lnt.Ed., 48, 8974-8977 (2009).
Song, Jie, et al., "Growth of endothelial cell on the surface of intravascular sent material: Bionic construction of bioactive extracellular matrix", Journal of Clinical Rehabilitative Tissue Engineering Research, 13(43), 8425-8431 (2009).
Sordella, R. et al., Gefitinib-Sensitizing EGFR Mutations in Lung Cancer Activate Anti-Apoptotic Pathways, Science, 305:1163-1167 (2004).
Subramanian, A. et al., Gene set enrichment analysis: A knowledge-based approach for interpreting genome-wide expression profiles, Proceedings of the National Academy of Sciences of the USA, 102(43):15545-15550 (2005).
Sun, T. et al., Activation of Multiple Proto-oncogenic Tyrosine Kinases in Breast Cancer via Loss of the PTPN12 Phosphatase, Cell, 144:703-718 (2011).
Tang, et al., "Adhesion and endothelialization of endothelial cells on the surface of endovascular stents by the novel rotational culture of cells," Applied Surface Science, 255:315-319 (2008).
Tang, et al., "In Vitro Gene Delivery by Degraded Polyamidoamine Dendrimers" Bioconjugate Chem. 7:703-714 (1996).
Turner, J.G. et al., ABCG2 expression, function, and promoter methylation in human multiple myeloma, Blood, 108(12):3881-3889 (2006).
Uhrich, K., "Hyperbranched Polymers for Drug Delivery" Trends Polym. Sci. 5: 388-393 (1997).
van de Wetering, et al., "Structure-Activity Relationships of Water-Soluble Cationic Methacrylate/Methacrylamide Polymers for Non viral Gene Delivery" Bioconjugate Chem. 10: 589-597 (1999).
Vittal et al., "Surfactant Promoted Enhancement on Electrochemical and Electrochromic Properties of Films of Prussian Blue and Its Analogs," Journal of the Electrochmical Socitey, 146(2):786-793 (1999).
Winer, E.P. et al., Optimizing Treatment of "Triple-Negative" Breast Cancer. SABCS 2007: Improving Outcomes in Advanced and Metastatic Breast Cancer, http://www.medscape.org/viewarticle/569483 (2007).
Woeblecke, H. et al., Reversal of breast cancer resistance protein-mediated drug resistance by tryprostatin A, International Journal of Cancer, 107:721-728 (2003).
Wood, E.R. et al., A Unique Structure for Epidermal Growth Factor Receptor Bound to GW572016 (Lapatinib): Relationships among Protein Conformation, Inhibitor Off-Rate, and Receptor Activity in Tumor Cells, Cancer Research, 64:6652-6659 (2004).
Yang, et al., "A New Approach to Identifying Genotoxic Carcinogens: p53 Induction as an Indicator ofGenotoxic Damage" Carcinogenesis, 19: P1117-P1125 (1998).
Yoon, C-H. et al., Activation of p38 Mitogen-Activated Protein Kinase Is Required for Death Receptor-Independent Caspase-8 Activation and Cell Death in Response to Sphingosine, Molecular Cancer Research, 7(3):361-370 (2009).
Zauner, et al., "Polylysine-Based Transfection Systems Utilizing Receptor-Mediated Delivery" Adv. Drug. Del. Rev. 30: 97-113 (1998).
Zhang, J., et al., "Multilayered Thin Films that Sustain the Release of Functional DNA under Physiological Conditions," 20(19): 8015-8021 (2004).
European Search Report of 08771046.3, dated Oct. 22, 2012, 4 pages.
International Preliminary Report on Patentability for PCT/US08/66948: entitled: Self Assembled Films for Protein and Drug Delivery Applications: Date of Issuance: Dec. 17, 2009.
International Search Report for PCT/US08/66948: entitled: Self Assembled Films for Protein and Drug Delivery Applications: Date of Mailing: Aug. 29, 2008.
International Preliminary Examination Report for PCT/US2002/34191, entitled: Methods of Making Decomposable Thin Films of Polyelectrolytes and Uses Thereof, Date of completion of report: Sep. 11, 2003.
International Search Report for PCT/US2002/34191, entitled: Methods of Making Decomposable Thin Films of Polyelectrolytes and Uses Thereof, Date mailed: Jan. 17, 2003.
International Preliminary Report on Patentability and Written Opinion for PCT/US2006/004295, entitled: Electrochemically Degradable Layer-By-Layer Thin Films, Date of Issuance: Aug. 7, 2007.
International Search Report for PCT/US2006/004295, entitled: Electrochemically Degradable Layer-By-Layer Thin Films, Date of Issuance: Oct. 2, 2006.
International Search Report for PCT/US2007/069937,entitled: Methods of Making Decomposable Thin Films of Polyelectrolytes and Uses Thereof, Date of mailing: Aug. 13, 2008.
International Preliminary Report on Patentability for PCT/US2007/069937, entitled: Methods of Making Decomposable Thin Films of Polyelectrolytes and Uses Thereof, Date of Issuance: Dec. 3, 2008.
International Preliminary Report on Patentability for PCT/US2007/69964, entitled: Methods of Making Decomposable Thin Films of Polyelectrolytes and Uses Thereof, Date of Issuance: Dec. 3, 2008.
International Search Report and Written Opinion for PCT/US2007/69964, entitled: Methods of Making Decomposable Thin Films of Polyelectrolytes and Uses Thereof, Date of Issuance: Oct. 29, 2007.
International Search Report for PCT/US2009/054011, entitled: Controlled Delivery of Bioactive Agents From Decomposable Films: Date of mailing: Nov. 24, 2010.
International Preliminary Report on Patentability for PCT/US2011/035057, entitled: Drug Deliver Coating and Devices, Date of issuance: Nov. 6, 2012.
International Search Report for PCT/US2011/035057, entitled: Drug Deliver Coating and Devices, Date of mailing: Feb. 8, 2012.
International Preliminary Report on Patentability for PCT/US2013/022430, entitled: Compositions and Methods for Coating, Date of issuance: Jul. 22, 2014.
International Search Report for PCT/US2013/022430, entitled: Compositions and Methods for Coating, Date of Mailing: May 15, 2013.
International Preliminary Report on Patentability and Written Opinion for PCT/US2012/035689, entitled: Coating Compositions, Methods and Coated Devices, Date of Issuance: Oct. 29, 2013.
International Search Report for PCT/US2012/035689, entitled: Coating Compositions, Methods and Coated Devices, Date of Mailing: Jul. 31, 2012.
International Preliminary Report on Patentability for PCT/US2012/035692, entitled: Coating Compositions, Methods and Coated Devices, Date of Issuance: Oct. 29, 2013.
International Search Report for PCT/US2012/35692, entitled: Coating Compositions, Methods and Coated Devices, Date of Mailing: Oct. 5, 2012.
International Search Report for PCT/US2013/066980, entitled: Devices and Methods for Layer-byLayer Assembly, Date of Mailing: Apr. 30, 2014.

(56) References Cited

OTHER PUBLICATIONS

International Search Report for PCT/US2013/37868, entitled: Compositions and Methods of Treatment of Drug Resistant Cancers, Date of Mailing: Sep. 6, 2013.
International Search Report for PCT/US2013/37869, entitled: Stable Layer-By-Layer Coated Particles, Date of Mailing: Sep. 13, 2013.
International Search Report for PCT/US2014/018284, entitled: Nucleic Acid Particles, Methods and Use Thereof, Date of mailing: Jul. 30, 2014.
International Search Report for PCT/US2014/022107, entitled: Compositions and Methods for Nucleic Acid Delivery, Date of mailing: Jun. 5, 2014.
Office Action for U.S. Appl. No. 13/115,107, entitled: "Multilayer Coating Compositions, Coated Substrates and Methods Thereof", Dated: Apr. 17, 2014.
Office Action for U.S. Appl. No. 12/542,267, entitled: "Controlled Delivery of Bioactive Agents From Decomposable Films", Dated: Mar. 31, 2014.
Office Action for U.S. Appl. No. 12/542,267, entitled: "Controlled Delivery of Bioactive Agents From Decomposable Films", Dated: Jun. 7, 2013.
Office Action for U.S. Appl. No. 12/542,267, entitled: "Controlled Delivery of Bioactive Agents From Decomposable Films", Dated: Aug. 17, 2012.
Office Action for U.S. Appl. No. 12/139,151, entitled: "Self Assembled Films for Protein and Drug Delivery Applications", Dated: Jun. 11, 2014.
Office Action for U.S. Appl. No. 12/139,151, entitled: "Self Assembled Films for Protein and Drug Delivery Applications", Dated: Jun. 20, 2012.
Office Action for U.S. Appl. No. 12/139,151, entitled: "Self Assembled Films for Protein and Drug Delivery Applications", Dated: Sep. 22, 2011.
Office Action for U.S. Appl. No. 11/459,979, entitled: "Methods of Making Decomposable Thin Films of Polyelectrolytes and Uses Thereof", Dated: Jul. 23, 2010.
Office Action for U.S. Appl. No. 11/459,979, entitled: "Methods of Making Decomposable Thin Films of Polyelectrolytes and Uses Thereof", Dated: Oct. 29, 2009.
Office Action for U.S. Appl. No. 11/815,718, entitled: "Electrochemically Degradable Layer-By-Layer Thin Films", Dated: Mar. 27, 2014.
Office Action for U.S. Appl. No. 11/815,718, entitled: "Electrochemically Degradable Layer-By-Layer Thin Films", Dated: Nov. 27, 2012.
Office Action for U.S. Appl. No. 11/815,718, entitled: "Electrochemically Degradable Layer-By-Layer Thin Films", Dated: Mar. 26, 2012.
Office Action for U.S. Appl. No. 10/280,268, entitled: "Methods of Making Decomposable Thin Films of Polyelectrolytes and Uses Thereofs", Dated: Nov. 2, 2004.
Office Action for U.S. Appl. No. 10/280,268, entitled: "Methods of Making Decomposable Thin Films of Polyelectrolytes and Uses Thereofs", Dated: Jul. 6, 2005.
Office Action for U.S. Appl. No. 10/280,268, entitled: "Methods of Making Decomposable Thin Films of Polyelectrolytes and Uses Thereofs", Dated: Jun. 29, 2006.

* cited by examiner

1A

α-cyclodextrin

β-cyclodextrin

γ-cyclodextrin generic β-cyclodextrin

1B poly 1 poly 2 poly 3

7A

7B

Prednisolone

Pilocarpine

Propofol

9A

9B

9C

11A

11B

12A

12B

13A

13B

14A

14B

14C

Flurbirprofen

Diclofenac

Naproxen

Ketoprofen

16A

16B

CONTROLLED DELIVERY OF BIOACTIVE AGENTS FROM DECOMPOSABLE FILMS

RELATED REFERENCES

This application claims priority to U.S. provisional patent application Ser. No. 61/089,560, filed Aug. 17, 2008, the entire contents of which are herein incorporated by reference.

GOVERNMENT FUNDING

The work described herein was made under grant number 5-R01-AG029601-03 awarded by the National Institutes of Health. The Government of the United States has certain rights in this application.

BACKGROUND

Layer-by-layer (LbL) assembly, a directed assembly technique based on complementary chemical interactions, can create nanoscale, conformal films with a broad range of therapeutics. LBL adsorption of oppositely charged polyelectrolytes on substrates can be used to fabricate thin multi-layer films for controlled release of bioactive agents such as drugs. Nevertheless, LbL-based methods of delivering drugs have been traditionally based on the formation of uniform films from which drugs escape via diffusion. Such diffusion-based release can limit or eliminate the opportunity for controlled sequential delivery of drugs released from the surface to the surrounding medium. With such films, a typical diffusive, nonlinear drug release pattern is typically observed, and rarely is diffusion-controlled release from LbL films sustained for more than a few hours. Also, processing methods for such films may involve harsh solvents, in addition to acidic byproducts of degradation, which may destroy the agent intended to be delivered.

Controlled release may be achieved using decomposable thin films comprising multilayer units comprised of polymer layers of alternating charge. Bioactive agents are released in a controlled fashion from the films as layers of polymers degrade.

SUMMARY

Controlled release of hydrophobic small molecules can be challenging. Certain barriers hamper the incorporation and release of such small molecules into decomposable LbL films, since small molecules may not have the charge density necessary for them to readily adsorb onto layers of polyelectrolytes. Disclosed herein a systems for controlled release of bioactive agents from LBL thin film coatings using a polymer comprising cyclodextrins. Cyclodextrins in the film coatings may serve as a carrier for hydrophobic small molecules. Undesired out-diffusion for release of small molecules is prevented through the use of polycyclodextrins. Sequential degradation of decomposable layers of LbL films allows small molecules to be released in a controlled manner.

Materials and methods provided herein may be particularly useful in drug applications. Applications in the food and cosmetic industries and in household items are also contemplated.

In certain embodiments, the disclosure provides a decomposable thin film comprising a plurality of multilayer units comprising a first layer having a first charge and a second layer having a second charge. In such decomposable thin films, at least a portion of the multilayers includes a polymer comprising a cyclodextrin backbone and/or a cyclodextrin as a pendant group associated with a bioactive agent. Decomposition of the thin film is characterized by sequential removal of at least a portion of the layers having the first charge and degradation of layers having the second charge and by release of the bioactive agent from the corresponding layer. The decomposable thin film comprises at least one degradable polyelectrolyte layer, wherein the degradable polyelectrolyte is hydrolyzable.

In some embodiments, the thin film comprises alternating cationic and anionic layers, and decomposition of the thin film is characterized by hydrolytic degradation of at least a portion of a layer selected from the group consisting of the cationic layers, the anionic layers, and both.

In some embodiments, the cyclodextrin is selected from the group consisting of α-cyclodextrins, β-cyclodextrins, γ-cyclodextrins, derivatives thereof, and combinations thereof. The cyclodextrin can be a derivatized or a modified cyclodextrin.

In some embodiments, at least one of the cyclodextrin molecules form a complex with the bioactive agent; in some such embodiments, the complex is an inclusion complex.

The bioactive agent may be a hydrophobic molecule. In some embodiments, the bioactive agent has a largest dimension less than about 0.9 nm, about 0.7 nm, or about 0.6 nm. In some embodiments, a portion of the bioactive agent has a largest dimension less than about 0.9 nm, about 0.7 nm, or about 0.6 nm.

In some embodiments, the bioactive agent is a Class II or Class IV compound (both of which are poorly soluble compounds) according to the Biopharmaceutical Classification System. The bioactive agent may be any of variety of drugs, including, but not limited to, anti-inflammatory drugs, anti-cancer drugs, antibiotics, anti-coagulants, anesthetics, and anti-glaucoma drugs.

In some embodiments, the bioactive agent is a food flavoring agent.

Polyelectrolytes may be synthetic, natural, or a both. In some embodiments, the polymer is a polyester, polyanhydride, polyorthoester, polyphosphazene, polyphosphoester, or combination thereof. In some embodiments, the polyester is a poly(β-amino ester); in some such embodiments, the polymer has a general structure

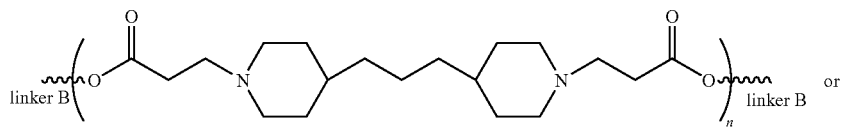

-continued

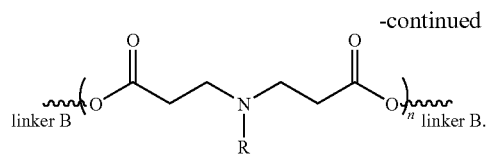

In certain embodiments, the poly(β-amino esters) may readily be prepared by condensing bis(secondary amines) or primary amines with bis(acrylate esters).

Degradation of the layers in the film may be in some embodiments hydrolytic, thermal, enzymatic, and/or photolytic. In some embodiments, at least a portion of the degradable polyelectrolyte layers comprises a biodegradable polymer.

In some embodiments, the film is deposited on a substrate that may or may not be planar. The substrate may be any of a variety of shapes and comprised of any of a variety of materials.

In certain embodiments, provided are methods of releasing a bioactive agent from a thin film comprising: providing a decomposable thin film comprising a plurality of multilayers including a first layer having a first charge and a second layer having a second charge, wherein at least one of the layers includes a polymer comprising a cyclodextrin backbone and/or a cyclodextrin as a pendant group. In such methods, the bioactive agent is associated with cyclodextrins in at least one of the layers, and the decomposable thin film includes at least one degradable polyelectrolyte layer, wherein the degradable polyelectrolyte is hydrolyzable. Such methods further comprise a step of placing the thin film in a medium in which at least a portion of the thin film decomposes via the substantially sequential removal of at least a portion of the layers having the first charge and degradation of layers having the second charge.

Provided methods all release of bioactive agents over a span of at least 2, at least 5, at least 10, and at least 12 days in various embodiments.

Definitions

"About" and "approximately:" As used herein, the terms "about" and "approximately," when used in reference to a number, include numbers that fall within a range of 20%, 10%, 5%, or 1% in either direction (greater than or less than) the number unless otherwise stated or otherwise evident from the context (except where such number would exceed 100% of a possible value).

"Bioactive agents": as used herein, "bioactive agents" refers to compounds or entities that alter, inhibit, activate, or otherwise affect biological or chemical events. For example, bioactive agents may include, but are not limited to, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anti-coagulants and/or antithrombotic agents, local anesthetics, ophthalmics, prostaglandins, anti-depressants, anti-psychotic substances, anti-emetics, and imaging agents. In some embodiments, the bioactive agent is a drug. In some embodiments, the bioactive agent is a small molecule.

Biological or chemical events that can be altered, inhibited, activated, or otherwise affected include those events that are involved in sensory perception. Bioactive agents therefore may also include compounds that are perceptible by a biological sensory system. Compounds that can be detected by one of the sensory systems of an animal, such as food flavoring agents (detectable by taste sensory systems), odorific compounds (detectable by olfactory sensory systems), and pheromones (detectable by pheromone-sensory systems) are included in the defintion of "bioactive agents."

A more complete listing of bioactive agents and specific drugs suitable for use may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, and the United States Pharmacopeia-25/National Formulary-20, published by the United States Pharmcopeial Convention, Inc., Rockville Md., 2001, all of which are incorporated herein by reference.

"Biomolecules": The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

"Biocompatible": The term "biocompatible", as used herein is intended to describe materials that do not elicit a substantial detrimental response in vivo.

"Biodegradable": As used herein, "biodegradable" polymers are polymers that degrade fully under physiological or endosomal conditions. In preferred embodiments, the polymers and biodegradation byproducts are biocompatible. Biodegradable polymers are not necessarily hydrolytically degradable and may require enzymatic action to fully degrade.

"Complex": The term "complex," as used herein, refers to a molecular entity formed by loose assication involving two or more component molecular entities (which can be ionic or uncharged). Bonding between components that are complexed together is typically weaker than in a covalent bond. In some embodiments, complexes are inclusion complexes (also known as "inclusion compounds") in which one chemical entity ("the host") forms a cavity in which one or more molecules of a second "guest" compound are located. For example, cyclodextrins can enclose and complex with a bioactive agent such as a small molecule drug, forming a cyclodextrin-drug inclusion complex.

"Cyclodextrin": The term "cyclodextrin," as used herein, refer to cyclic oligoglucosides containing between 5 to about 10 (inclusive) glucose residues in which an enclosed tubular space allows reception of a guest molecule. The term "cyclodextrin" has also been used synonymously with "Schardinger dextrin."

"Degradation": The phrase "degradation", as used herein, relates to the cleavage of a covalent polymer backbone. Full degradation of a polymer breaks the polymer down to monomeric species.

"Endosomal conditions": The phrase "endosomal conditions", as used herein, relates to the range of chemical (e.g., pH, ionic strength) and biochemical (e.g., enzyme concentrations) conditions likely to be encountered within endosomal vesicles. For most endosomal vesicles, the endosomal pH ranges from about 5.0 to 6.5.

"Hydrolytically degradable": As used herein, "hydrolytically degradable" polymers are polymers that degrade fully in the sole presence of water. In preferred embodiments, the polymers and hydrolytic degradation byproducts are biocompatible. As used herein, the term "non-hydrolytically degradable" refers to polymers that do not fully degrade in the sole presence of water.

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

"Polyelectrolyte" or "polyion": The terms "polyelectrolyte" or "polyion", as used herein, refer to a polymer which under some set of conditions (e.g., physiological conditions) has a net positive or negative charge. Polycations have a net positive charge and polyanions have a net negative charge. The net charge of a given polyelectrolyte or polyion may depend on the surrounding chemical conditions, e.g., on the pH.

"Polynucleotide", "nucleic acid", or "oligonucleotide": The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least three nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Polypeptide", "peptide", or "protein": According to the present application, a "polypeptide", "peptide", or "protein" comprises a string of at least three amino acids linked together by peptide bonds. The terms "polypeptide", "peptide", and "protein", may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide. The phrase "enzyme polypeptide" refers to a polypeptide having enzymatic activity.

"Polysaccharide", "carbohydrate" or "oligosaccharide": The terms "polysaccharide", "carbohydrate", or "oligosaccharide" refer to a polymer of sugars. The terms "polysaccharide", "carbohydrate", and "oligosaccharide", may be used interchangeably. Typically, a polysaccharide comprises at least three sugars. The polymer may include natural sugars (e.g., glucose, fructose, galactose, mannose, arabinose, ribose, and xylose) and/or modified sugars (e.g., 2'-fluororibose, 2'-deoxyribose, and hexose).

"Small molecule": As used herein, the term "small molecule" is used to refer to molecules, whether naturally-occurring or artificially created (e.g., via chemical synthesis), that have a relatively low molecular weight. Typically, small molecules are monomeric and have a molecular weight of less than about 1500 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered acceptable for use in accordance with the present application.

Acronyms

The following acronyms are used herein: "SPS" is poly (styrene sulfonate), "PAA" is poly(acrylic acid), "LPEI" is linear poly(ethylene imine), "PDAC" is poly(diallyl dimethyl ammonium chloride), "PAH" is poly(allylamine hydrochloride), and "PAZO" is the azobenzene functionalized polymer poly{1-[4-(3-carboxy-4-hydroxyphenylazo) benzensulfonamido]-1,2-ethanediyl}.

BRIEF DESCRIPTION OF THE FIGURES

FIG. 1A depicts representative chemical structures of α-, β-, and γ-cyclodextrins and of generic structure of β-cyclodextrins showing sites of possible substitutions (R groups). FIG. 1B illustrates a LBL platform, where LBL assembly and supramolecular chemistry are used to create an ultrathin film platform technology for small molecule delivery using a hydrolytically degradable polyion and polymeric cyclodextrin.

In FIG. 4A, normalized amounts of release is plotted at various timepoints. In FIG. 4B, film height is plotted at various timepoints. Decreased film height over time may represent film degradation.

In FIG. 5A, normalized amounts of release is plotted at various timepoints. In FIG. 5B, film height is plotted at various timepoints. Decreased film height over time may represent film degradation.

FIG. 7A illustrates a schematic for layer-by-layer assembly of films for tunable release of bioactive agents. Alternating layers of polyanion and polycation are deposited onto a substrate such as a slide by dipping alternately into polyanion and polycation solutions. Hydrolytic degradation of polymer layers allow controlled and possibly sequential release of bioactive agents. In FIG. 7B, the left side shows film components. Three poly(β-amino esters) were investigated as degradable polycation. Poly(carboxymethylbetacyclodextrin) was used as the anionic supramolecular complex. The right side shows electrostatic assembly; the light color is water. The bottom portion shows molecules used in experimentation.

FIG. 9B depicts amount of Dexamethasone released from the film over time. Stability of Poly 1/Captisol-Dexamethasone films is depicted in FIG. 9C, which shows the fraction of the film (by thickness) remaining over time.

In FIG. 13A, drug diffuses out of the film without cyclodextrin; drug release is uncontrolled. In FIG. 13B, drug is being released inside a cyclodextrin in a controlled manner consistent with surface erosion of the polymer layers.

FIG. 14A depicts the emission spectra of prodan in various solvents. Note that its emission spectrum shifts depending on the polarity of the solvent. FIG. 14B depicts the emission spectra of prodan in water (the curve on the right) and in BCD (the curve on the left). FIG. 14C depicts the emission spectra of prodan released from (Poly 1/poly (BCD)-prodan)$_{20}$ films after 0.83, 3.5, and 16 hours in solution.

In FIG. 16A, total amount of released drug is plotted against time. In FIG. 16B, normalized amount of released drug was plotted against time. Amount of released drug was normalized by dividing by the total amount of drug released at the last timepoint measured.

DETAILED DESCRIPTION OF CERTAIN EMBODIMENTS

Figure 1:
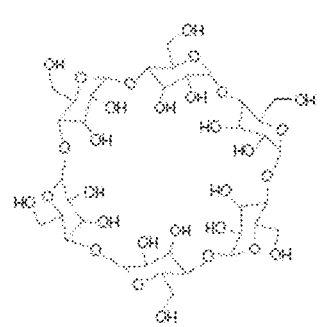
FIG. 1A and FIG. 1B represent cyclodextrin and the LBL film.
Figure 1:
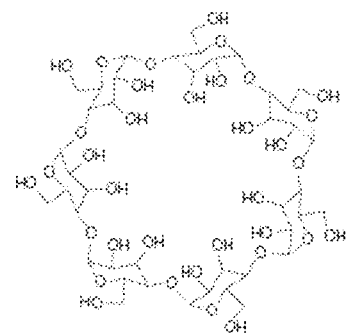
Figure 1:
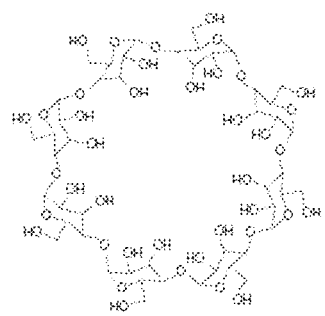
Figure 1:
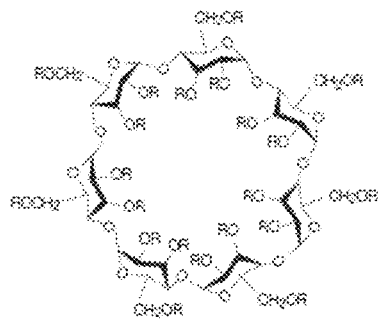
Figure 1:
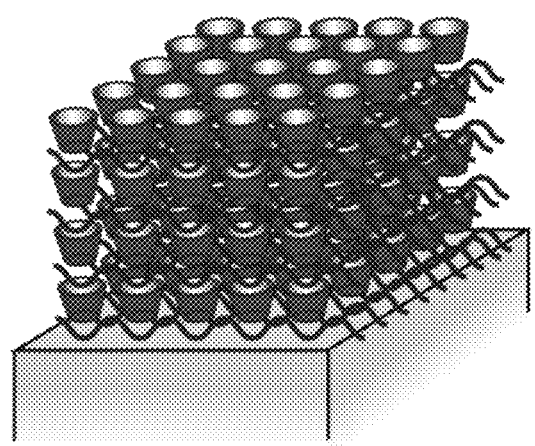

In various embodiments, systems for incorporating uncharged bioactive agents (including those having therapeutic value) into layer-by-layer films that allow controlled release are disclosed. Control may be achieved over dose, release rate, and/or time span.

Decomposable Films

Decomposition of the thin films is characterized by the substantially sequential degradation of at least a portion of the polyelectrolyte layers that make up the thin films. The degradation may be at least partially hydrolytic, at least partially enzymatic, at least partially thermal, and/or at least partially photolytic. In some embodiments, the thin films are about 1 nm and about 100 µm thick, for example, between about 1 nm and about 100 nm thick, between about 100 nm and about 1 µm thick, between about 1 µm and about 10 µm thick, or between about 10 µm and about 100 µm thick.

Films are generally comprised of alternating layers of surface erodible polyelectrolytes (such as degradable polymers)

and bioactive agents that are associated with charged polymeric cyclodextrins. Generally, the bioactive agents are hydrophobic small molecules. The film may be comprised of multilayer units with alternating layers of opposite charge, such as alternating anionic and cationic layers. For example, a cationic polyelectrolyte may be layered next to an anionic layer comprising polymeric cyclodextrin-bioactive agent complexes. At least one of the layers in a multilayer unit includes a degradable polyelectrolyte. As an example, the film may be comprised of an at least partially degradeable polycationic layer and a polyanionic layer comprising polymeric cyclodextrin-bioactive agent complexes.

The thin film may be exposed to a liquid medium (e.g., intracellular fluid, interstitial fluid, blood, intravitreal fluid, intraocular fluid, gastric fluids, etc.), whereupon the polycationic layers degrade and the polyanionic layers delaminate sequentially from the surface toward the substrate. Bioactive agents are thus gradually and controllably released from the surface of the thin film.

It will be appreciated that the roles of the layers of the thin film can be reversed. In such embodiments, the polyanionic layers include a degradable polyanion and the polycationic layers may include, for example, a cationic cyclodextrin. Alternatively, the polycationic and polyanionic layers may both include degradable polyelectrolytes.

Degradable polyelectrolytes and their degradation byproducts may be biocompatible so as to make the films amenable to use in vivo.

Assembly Methods

In certain embodiments, the LbL assembly of films may involve a series of dip coating steps in which the substrate is dipped in alternating polycationic and polyanionic solutions. Additionally or alternatively, it will be appreciated that deposition of alternating polycationic and polyanionic layers may also be achieved by spray coating, brush coating, roll coating, spin casting, or combinations of any of these techniques.

In certain embodiments, multiple layers of oppositely charged polymers are deposited on a charged surface from aqueous baths in a highly controllable process. Bioactive agents can be incorporated into individual layers of the film, affording the opportunity for exquisite control of loading and release from the film. There are several advantages to this technique, including mild aqueous processing conditions (which may allow preservation of biomolecule function); nanometer-scale conformal coating of surfaces; and the flexibility to coat objects of any size, shape or surface chemistry, leading to versatility in design options.

Substrates for Constructing Films

A variety of materials can be used as substrates such as, but not limited to, metals, e.g., gold, silver, platinum, and aluminum; metal-coated materials; metal oxides; plastics; ceramics; silicon; glasses; mica; graphite; hydrogels; and polymers such as polyamides, polyphosphazenes, polypropylfumarates, polyethers, polyacetals, polycyanoacrylates, polyurethanes, polycarbonates, polyanhydrides, polyorthoesters, polyhydroxyacids, polyacrylates, ethylene vinyl acetate polymers and other cellulose acetates, polystyrenes, poly(vinyl chloride), poly(vinyl fluoride), poly(vinyl imidazole), poly(vinyl alcohol), poly(ethylene terephthalate), polyesters, polyureas, polypropylene, polymethacrylate, polyethylene, poly(ethylene oxide)s and chlorosulphonated polyolefins; and combinations thereof. For example, a substrate of one material may be coated with a second material, or two materials may be combined to form a composite.

It will be appreciated that materials with an inherently charged surface are particularly attractive substrates for LbL assembly of a thin film. Alternatively, a range of methods are known in the art that can be used to charge the surface of a material, including but not limited to plasma processing, corona processing, flame processing, and chemical processing, e.g., etching, micro-contact printing, and chemical modification. For example, plastics can be used as substrates, particularly if they have been chemically modified to present polar or charged functional groups on the surface. Additionally or alternatively, substrates can be primed with specific polyelectrolyte bilayers such as, but not limited to, LPEI/SPS, PDAC/SPS, PAH/SPS, LPEI/PAA, PDAC/PAA, and PAH/PAA bilayers, that form readily on weakly charged surfaces and occasionally on neutral surfaces. It will be appreciated that primer layers provide a uniform surface layer for further LBL assembly and are therefore particularly well suited to applications that require the deposition of a uniform thin film on a substrate that includes a range of materials on its surface, e.g., an implant (such as stent) or a complex tissue engineering construct.

The substrate geometry may be manipulated to deposit films having a variety of shapes. For example, films may be deposited on particles, tubes, or spheres to facilitate a more uniform release distribution. Films may be deposited on strands such as sutures to release factors such as analgesics or antibiotics at a surgical site; coiled strands may also serve as substrates. Alternatively, these films may be deposited onto capillary networks or tissue engineering constructs. For example, a thin film deposited on a three-dimensional tissue engineering construct may be used to attract cells to a newly implanted construct and then to promote specific metabolic or proliferative activity. As another example, a thin film may be deposited on an intraocular lens to release bioactive agents that relieve and/or treat ocular conditions (such as ocular inflammation). Lens-shaped substrates may be any of a variety of shapes, including opthalmic (convex-concave), biconvex, plano-convex, meniscus, plano-concave, and biconcave.

Methods herein may also be used to create three-dimensional microstructures. For example, the thin film may be deposited on a substrate that can be dissolved to leave a hollow shell of the thin film. Alternatively or additionally, multi-layers may be deposited on substrates having regions that are more and less degradable. Degradation of the degradable portions leaves a three-dimensional microstructure. In a first step, the surface of a substrate is divided into regions in which LbL deposition of an inventive thin film is more or less favorable. In one embodiment, a pattern of self-assembled monolayers (SAMs) is deposited on a substrate surface by microcontact printing (see, for example, U.S. Pat. No. 5,512,131 to Kumar et al., see also Kumar et al., *Langmuir* 10:1498, 1994; Jiang and Hammond, *Langmuir,* 16:8501, 2000; Clark et al., *Supramolecular Science* 4:141, 1997; and Hammond and Whitesides, *Macromolecules* 28:7569, 1995). In some embodiments, the substrate surface is neutral and the exposed surface of the deposited SAMs is polar or ionic (i.e., charged). A variety of polymers with polar or ionic head groups are known in the art of self-assembled monolayers. In some embodiments, a uniform coating of a polymer is deposited on a substrate, and that coating is transformed into a patterned layer by means of photolithography. Other embodiments are also contemplated in which the substrate surface is selectively exposed to plasmas, various forms of electromagnetic radiation, or to electron beams. In yet other embodiments, the substrate may possess the desired surface characteristics by virtue of its inherent composition. For example, the substrate may be a composite in which different regions of the surface have differing compositions, and thus different affinities for the polyelectrolyte to be deposited.

In a second step, polyelectrolyte layers of alternating charge are deposited by LbL on receptive regions of the surface as described for a homogeneous surface above and for selective regions as described in Jiang and Hammond, *Langmuir*, 16:8501, 2000; Clark et al., *Supramolecular Science* 4:141, 1997; and Hammond and Whitesides, *Macromolecules* 28:7569, 1995. The surface is subsequently flooded with a non-degradable polymer and placed in a medium wherein at least a portion of the polyelectrolyte layers degrade, thereby creating a three-dimensional "tunnel-like" structure that reflects the pattern on the original surface. It will be appreciated that more complex microstructures could be created based on these simple principles (e.g., by depositing SAMs with different electrostatic character in different regions of a substrate surface and/or by iterative additions of subsequent structures above the deposited non-degradable polymer).

Degradable Polyelectrolytes

Any degradable polyelectrolyte can be used in the thin film disclosed herein, including, but not limited to, hydrolytically degradable, biodegradable, thermally degradable, and photolytically degradable polyelectrolytes. Hydrolytically degradable polymers known in the art include for example, certain polyesters, polyanhydrides, polyorthoesters, polyphosphazenes, and polyphosphoesters. Biodegradable polymers known in the art, include, for example, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine, poly(lactic acid) (PLA), poly(glycolic acid) (PGA), poly(caprolactone) (PCL), poly(lactide-co-glycolide) (PLG), poly(lactide-co-caprolactone) (PLC), and poly(glycolide-co-caprolactone) (PGC). Those skilled in the art will recognize that this is an exemplary, not comprehensive, list of biodegradable polymers. The properties of these and other polymers and methods for preparing them are further described in the art. See, for example, U.S. Pat. Nos. 6,123,727; 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. Nos. 4,806,621; 4,638,045 to Kohn; and U.S. Pat. No. 4,946,929 to d'Amore; see also Wang et al, *J. Am. Chem. Soc.* 123:9480, 2001; Lim et al., *J. Am. Chem. Soc.* 123:2460, 2001; Langer, *Acc. Chem. Res.* 33:94, 2000; Langer, *J. Control Release* 62:7, 1999; and Uhrich et al., *Chem. Rev.* 99:3181, 1999. Of course, co-polymers, mixtures, and adducts of these polymers may also be employed.

The anionic polyelectrolytes may be degradable polymers with anionic groups distributed along the polymer backbone. The anionic groups, which may include carboxylate, sulfonate, sulphate, phosphate, nitrate, or other negatively charged or ionizable groupings, may be disposed upon groups pendant from the backbone or may be incorporated in the backbone itself. The cationic polyelectrolytes may be degradable polymers with cationic groups distributed along the polymer backbone. The cationic groups, which may include protonated amine, quaternary ammonium or phosphonium-derived functions or other positively charged or ionizable groups, may be disposed in side groups pendant from the backbone, may be attached to the backbone directly, or can be incorporated in the backbone itself.

For example, a range of hydrolytically degradable amine containing polyesters bearing cationic side chains have recently been developed (Putnam et al. *Macromolecules* 32:3658-3662, 1999; Barrera et al. *J. Am. Chem. Soc.* 115: 11010-11011, 1993; Kwon et al. *Macromolecules* 22:3250-3255, 1989; Lim et al. *J. Am. Chem. Soc.* 121:5633-5639, 1999; Zhou et al. *Macromolecules* 23:3399-3406, 1990; each of which is incorporated herein by reference). Examples of these polyesters include poly(L-lactide-co-L-lysine) (Barrera et al. *J. Am. Chem. Soc.* 115:11010-11011, 1993; incorporated herein by reference), poly(serine ester) (Zhou et al. *Macromolecules* 23:3399-3406, 1990; which is incorporated herein by reference), poly(4-hydroxy-L-proline ester) (Putnam et al. *Macromolecules* 32:3658-3662, 1999.; Lim et al. *J. Am. Chem. Soc.* 121:5633-5639, 1999; each of which is incorporated herein by reference), and more recently, poly[α-(4-aminobutyl)-L-glycolic acid].

In addition, poly(β-amino ester)s, prepared from the conjugate addition of primary or secondary amines to diacrylates, are suitable for use. Typically, poly(β-amino ester)s have one or more tertiary amines in the backbone of the polymer, preferably one or two per repeating backbone unit. Alternatively, a co-polymer may be used in which one of the components is a poly(β-amino ester). Poly(β-amino ester)s are described in U.S. Pat. Nos. 6,998,115 and 7,427,394, entitled "Biodegradable poly(β-amino esters) and uses thereof" and Lynn et al., *J. Am. Chem. Soc.* 122:10761-10768, 2000, the entire contents of both of which are incorporated herein by reference.

In some embodiments, the polymer can have a formula below:

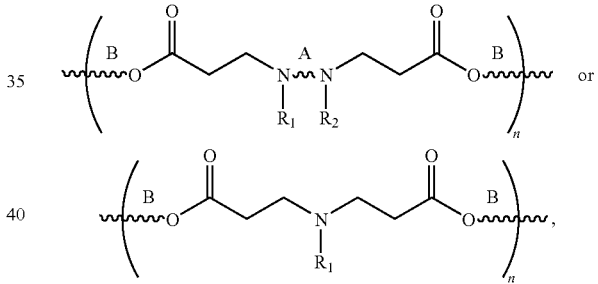

where A and B are linkers which may be any substituted or unsubstituted, branched or unbranched chain of carbon atoms or heteroatoms. The molecular weights of the polymers may range from 1000 g/mol to 20,000 g/mol, preferably from 5000 g/mol to 15,000 g/mol. In certain embodiments, B is an alkyl chain of one to twelve carbons atoms. In other embodiments, B is a heteroaliphatic chain containing a total of one to twelve carbon atoms and heteroatoms. The groups $R_1$ and $R_2$ may be any of a wide variety of substituents. In certain embodiments, $R_1$ and $R_2$ may contain primary amines, secondary amines, tertiary amines, hydroxyl groups, and alkoxy groups. In certain embodiments, the polymers are amine-terminated; and in other embodiments, the polymers are acrylated terminated. In some embodiments, the groups $R_1$ and/or $R_2$ form cyclic structures with the linker A.

Exemplary poly(β-amino esters) include

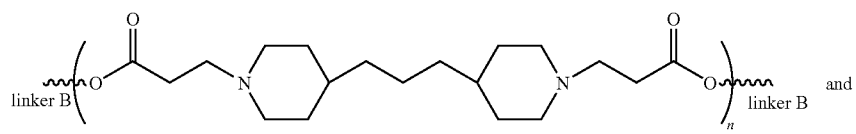

and

-continued

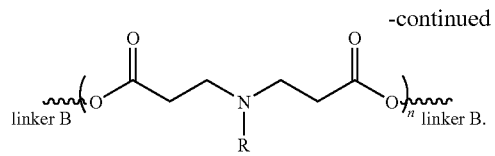

Exemplary R groups include hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups.

Exemplary linker groups B includes carbon chains of 1 to 30 carbon atoms, heteroatom-containing carbon chains of 1 to 30 atoms, and carbon chains and heteroatom-containing carbon chains with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups. The polymer may include, for example, between 5 and 10,000 repeat units.

In some embodiments, the poly(β-amino ester)s are selected from the group consisting of solved in THF) and the reaction mixture stirred with heat and under nitrogen to form polymers.

In some embodiments, the diacrylate monomers used in synthesis are selected from the group consisting of 1,3-propanediol diacrylate, 1,4-butanediol diacrylate, 1,6-hexanediol diacrylate, 1,9-nonanediol diacrylate, neopentyl glycol diacrylate, trimethylolpropane benzoate diacrylate, 2,2,3,3,4,4,5,5-Octafluoro-1,6-hexanediol diacrylate, trimethylolpropane ethoxylate methyl ether diacrylate, 1,4-cyclohexanedimethyl diacdrylate, and combinations thereof. (See FIG. 3 for structures of these monomers.)

Alternatively or additionally, zwitterionic polyelectrolytes may be used. Such polyelectrolytes may have both anionic and cationic groups incorporated into the backbone or covalently attached to the backbone as part of a pendant group. Such polymers may be neutrally charged at one pH, positively charged at another pH, and negatively charged at a third pH. For example, a film may be constructed by LbL deposition using dip coating in solutions of a first pH at which one layer is anionic and a second layer is cationic. If the film is put into a solution having a second different pH, then the first layer may be rendered cationic while the second layer is rendered anionic, thereby changing the charges on those layers.

The composition of the polyanionic and polycationic layers can be fine-tuned to adjust the degradation rate of each layer within the film. For example, the degradation rate of hydrolytically degradable polyelectrolyte layers can be decreased by associating hydrophobic polymers such as hydrocarbons and lipids with one or more of the layers. Alter-

Figure 2:
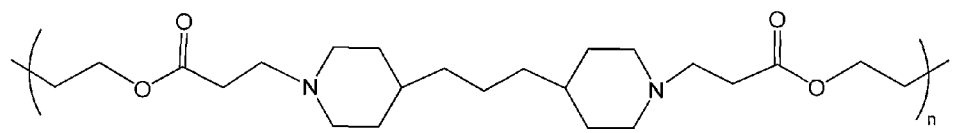
FIG. 2 depicts chemical structures of certain polymers that may be used. Shown are the structures for a poly 1, poly 2, and poly 3.
Figure 2:
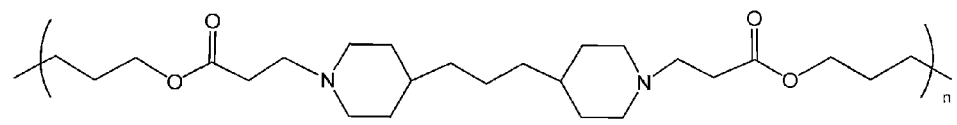
Figure 2:
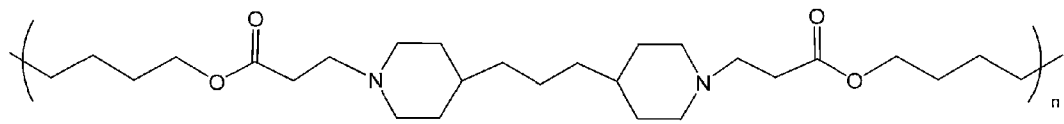

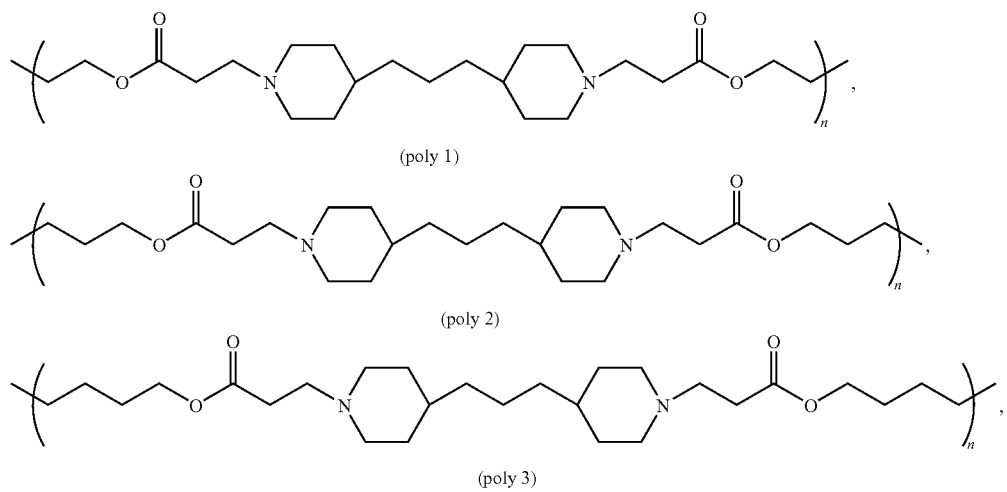

derivatives thereof, and combinations thereof. (See FIG. 2).

Figure 3:
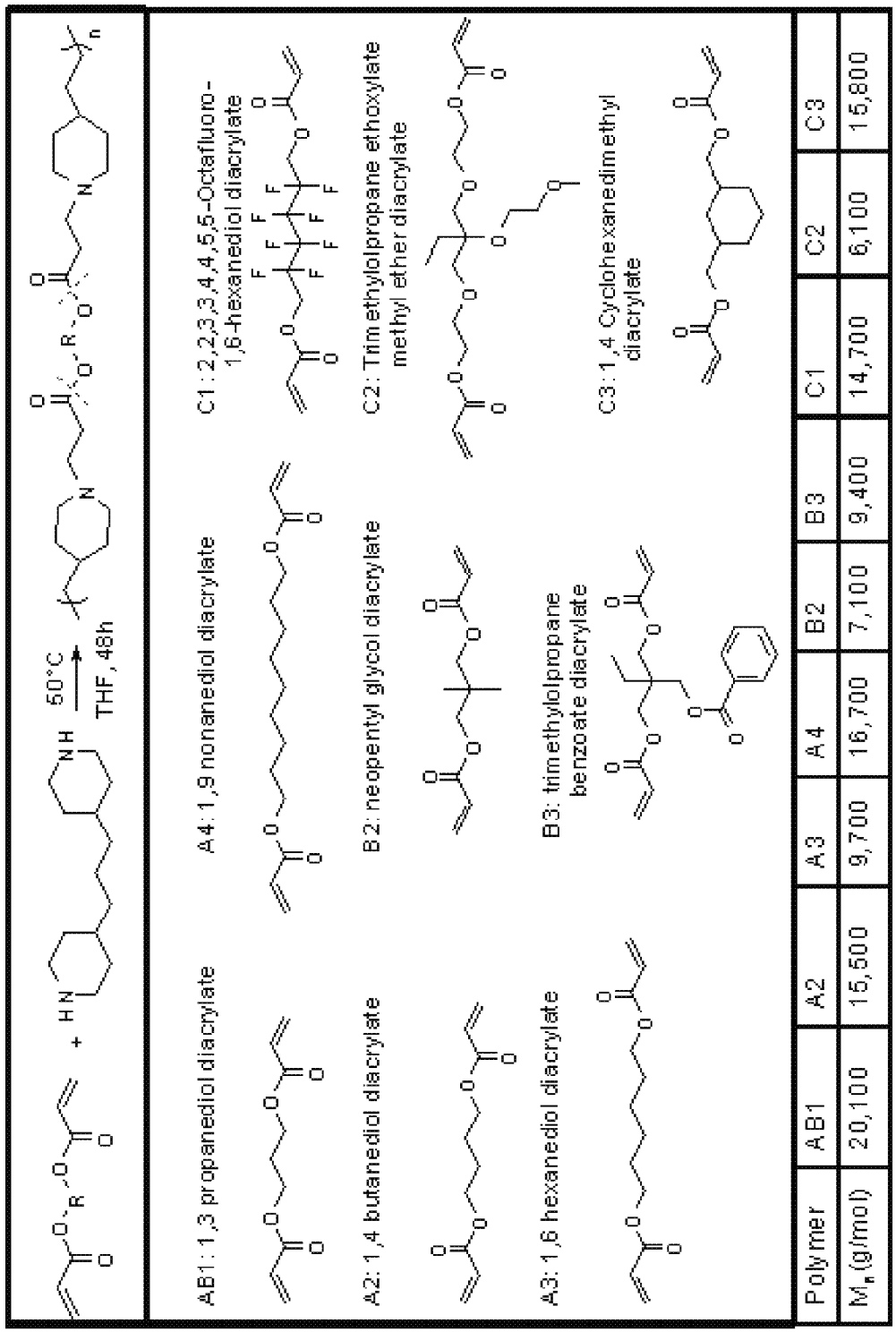
FIG. 3 illustrates a reaction scheme for the synthesis of poly (β-amino ester)s and the diacrylate monomers used. Dashed lines indicated hydrolyzable bonds. Letters are used to designate the categories of monomers investigated for effect on film characteristics. A refers alkyl chain length; B refers to steric bulk; and C refers to mechanism clarification. In categories A and B, increasing number corresponds to greater alkyl chain length or bulk, respectively. Polymer number average molecular weights ($M_n$) were determined via gel permeation chromatography.

In certain embodiments, the poly (β-amino ester) is synthesized from diacrylate monomers using a reaction scheme as outlined in FIG. 3. In an example of such a synthesis, a solution of 4,4-trimethylenedipiperidine in anhydrous THF is added to the diacrylate monomer (which may also be disnatively, the polyelectrolyte layers may be rendered more hydrophilic to increase their hydrolytic degradation rate. In certain embodiments, the degradation rate of a given layer can be adjusted by including a mixture of polyelectrolytes that degrade at different rates or under different conditions. In other embodiments, the polyanionic and/or polycationic layers may include a mixture of degradable and non-degradable polyelectrolytes. Any non-degradable polyelectrolyte can be used. Exemplary non-degradable polyelectrolytes that could be used in thin films include poly(styrene sulfonate) (SPS), poly(acrylic acid) (PAA), linear poly(ethylene imine) (LPEI), poly(diallyldimethyl ammonium chloride) (PDAC), and poly (allylamine hydrochloride) (PAH).

Alternatively or additionally, the degradation rate may be fine-tuned by associating or mixing non-biodegradable, yet biocompatible polymers (polyionic or non-polyionic) with one or more of the polyanionic and/or polycationic layers. Suitable non-biodegradable, yet biocompatible polymers are well known in the art and include polystyrenes, certain polyesters, non-biodegradable polyurethanes, polyureas, poly (ethylene vinyl acetate), polypropylene, polymethacrylate, polyethylene, polycarbonates, and poly(ethylene oxide)s.

Cyclodextrins

Films provided herein generally comprise layers of polymeric cyclodextrins, which can act as carriers for bioactive agents intended to be released from such films. Cyclodextrins (sometimes called cycloamyloses) are cyclic oligosaccharides containing α-D-glucopyranose units linked by α-1,4 glycosidic bonds. Common types of cyclodextrins include the α-cyclodextrins (comprised of 6 units), β-cyclodextrins (comprised of 7 units), and γ-cyclodextrins (comprised of 8 units). Other types of cyclodextrins include the δ-cyclodextrins (comprised of 9 units) and the ε-cyclodextrins (comprised of 10 units). Cyclodextrins comprising 5 or more than 10 glucopyranose units are also known and/or have been synthesized. For example, large cyclodextrins containing 32 1,4-anhydroglucopyranoside units have been characterized. Large cyclodextrins containing at least 150 glucopyranoside units are also known.

Because of the chair conformation of the glycopyranose units, cyclodextrins are generally toroidally shaped and shaped like a truncated cone. The cavities have different diameters depending on the number of glucose units. For example, the diameters of the cavities of empty cyclodextrin molecules (as measured as the distance between anomeric oxygen atoms) may be approximately for 0.56 nm for α-cyclodextrins, approximately 0.70 nm for β-cyclodextrins, or 0.88 for γ-cyclodextrins.

Hydrophilic groups are presented on the outside of the molecular cavity, whereas the inner surface of cyclodextrins are generally hydrophobic. The property enables cyclodextrins to host neutral and/or hydrophobic molecules by making inclusion compounds. Cyclodextrins are also particularly amenable to hosting hydrophobic small molecules.

Cyclodextrins that may be used include synthetic, naturally occurring, and modified cyclodextrins. Naturally occurring cyclodextrins are produced from starch by means of enzymatic conversion by cyclomaltodextrin glycanotransferase. Synthetic cyclodextrins include 5-membered macrocycles.

The hydroxyl groups may be substituted to alter the specificity, physical properties, and/or chemical properties of cyclodextrins. Substituent groups include, but are not limited to, methyl, hydroxyethyl, sulfobutylether, glucosyl, maltosyl, etc. A generic structure of a β-cyclodextrin is presented in FIG. 1. Table 1 presents list of commonly used β-cyclodextrin derivatives and identities of R groups in the generic structure of FIG. 1. It is to be understood that the following list is non-limiting, and that, furthermore, other cyclodextrins such as α- and γ-cyclodextrin may also be modified. For example, γ-cyclodextrin may be substituted with a hydroxypropyl group to yield 2-Hydroxypropyl-γ-cyclodextrin (HPγCD).

In addition to derivatives of cyclodextrins, combinations of different cyclodextrins may be used to construct films herein.

TABLE 1

Examples of cyclodextrin derivatives

| Cyclodextrin derivative | R group |
| --- | --- |
| Dimethyl-β-cyclodextrin (DMβCD) | —$CH_3$ or —H |
| Trimethyl-β-cyclodextrin (TMβCD) | —$CH_3$ |
| Randomly methylated-β-cyclodextrin (RMβCD) | —$CH_3$ or —H |
| Hydroxyethyl-β-cyclodextrin (HEβCD) | —$CH_2CH_2OH$ or —H |
| 2-Hydroxypropyl-β-cyclodextrin (HPβCD) | —$CH_2CHOHCH_3$ or —H |
| 3-Hydroxypropyl-β-cyclodextrin (3HPβCD) | —$CH_2CH_2CH_2OH$ or —H |
| 2,3-Dihydroxypropyl-β-cyclodextrin (DHPβCD) | —$CH_2CHOHCH_2OH$ or —H |
| 2-Hydroxyisobutyl-β-cyclodextrin (HIBβCD) | —$CH_2C(CH_3)_2OH$ or —H |
| Sulphobutylether-β-cyclodextrin (SBEβCD), (Captisol ®) | —$(CH_2)_4SO_3Na$ or —H |
| Carboxymethyl-β-cyclodextrin | —$CH_2COO^-$ |
| Glucosyl-β-cyclodextrin ($G_1$βCD) | -glucosyl or —H |
| Maltosyl-β-cyclodextrin ($G_2$βCD) | -maltosyl or —H |

Polymeric Cyclodextrins

Figure 10:
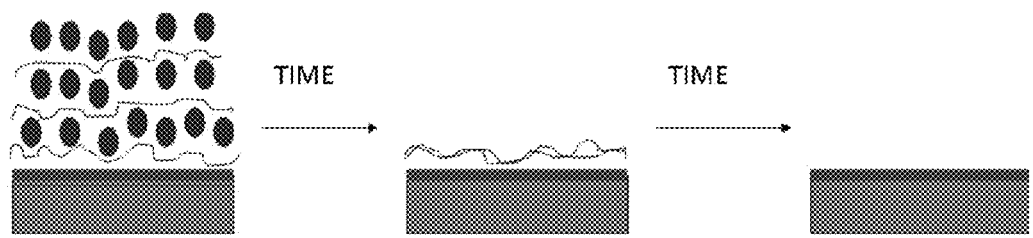
FIG. 10 depicts a possible mechanism of release for poly 1/Captisol films. The instantaneous, uncontrolled release of dexamethasone from such films is not due to polymer degradation, but rather, to instability of the films. The time scale of degradation is also too short to be consistent with a top down degradation mechanism.

Films can have a polymer comprising a cyclodextrin backbone and/or a cyclodextrin as a pendant group (i.e., polymeric cyclodextrins). Cyclodextrins of a variety of types may be used in polymeric form, including α-, β-, and γ-cyclodextrins. Modified cyclodextrins (such as, but not limited to, those listed in Table 1) may also be used in polymeric form. A representation of a polymeric cyclodextrin complexed with a drug is shown in FIG. 10.

Polymeric cyclodextrins may be synthesized by methods known in the art. (See, e.g., Martin et al. 2006. "Solubility and Kinetic Release Studies of Naproxen and Ibuprofen in Soluble Epichlorohydrin-β-cyclodextrin Polymer," *Supramolecular Chemistry.* 18(8): 627-631, the contents of which are herein incorporated by reference in their entirety). Examples of polymeric cyclodextrins include polymers of epi-chlorohydrin-β-cyclodextrin (β-CDEPI), carboxymethyl β-cyclodextrin (BCD), etc.

Polymeric cyclodextrins can be substituted with various groups or moieties, which can alter physical properties, and/ or chemical properties of the polymer. For example, solubility in water and/or charges of polymeric cyclodextrins may modified by substituent groups. Substitution can be associated with the polymer backbone or the pendant groups. In some embodiments, cylcodextrin is modified directly. In other embodiments, other portion of the polymer is modified with substituent groups. Variations of cyclodextrins have different solubilities may facilitate delivery of a wide range of bioactive agents. The ability to adjust charge type or density can be helpful for LBL film construction.

In some embodiments, the polymer types are crosslinked cyclodextrins. Some of these randomly crosslinked polymers are water soluble; for example, epichlorohydrin-crosslinked β-cyclodextrin has higher aqueous solubility than β-cyclodextrin. Additional exemplary polymeric cyclodextrins are described by Brewster et al. (Brewster et al., *Nature Reviews* (3), 1023-1035, 2004), which is incorporated herein by reference.

In addition to polymers having cyclodextrin backbone, polymers having cyclodextrins as pendant groups may also be used. These types of polymers can have various polymer backbones and functionalized cyclodextrins. The polymer backbone can have various lengths, molecular weight, charges and substituent groups as described above. Exemplary backbone polymers, including, but not limited to, polyacrylic esters, polyallylamines, polymethacrylates, chitosan, polyester, polyethlenimine, and dendrimers. In some embodiments, the backbone polymer can be degradable polymers as previously described. In certain embodiments, the polymer is a poly(β-amino esters), which is conjugated with cyclodextrins with or without additional linkers and/or functional groups. The number of cyclodextrin per repeat unit in the polymer can also be readily adjust for practical use. For example, the higher density of cyclodextrins in the polymer, the larger loading capacity the polymer theoretically has.

Bioactive Agents

Bioactive agents that can be incorporated into films include, but are not limited to small molecules that may act as therapeutics, food flavoring agents, odorants, pheromones, etc. Provided systems are particularly useful for incorporating hydrophobic small molecules (which typically have little or no surface charge) into degradable LbL films and for controlled release of such small molecules. Sizes of bioactive agents that are amenable for use include those having largest dimensions less than about 0.9 nm, less than about 0.7, and less than about 0.6 nm.

Controlled release of small molecule drugs may be achieved using the disclosed systems. Any drug that may be associated with cyclodextrin molecules, such as in an inclusion complex, may potentially be released in a controlled manner using methods and films disclosed herein.

Some classes of compounds may be particularly suitable for use. The Biopharmaceutical Classification System (BCS) divides drugs and drug candidates into four classes based on their solubility and permeability characteristics. Class I compounds are soluble, permeable drugs whose oral bioavailability are only limited by the rate at which they reach appropriate sites of absorption in the gastrointestinal (GI) tract. Class II drugs are poorly soluble but permeable through the gut; oral adsorption of Class II compounds is limited by drug solubility and dissolution rate. Class III compounds are soluble but poorly permeable. That is, oral bioavailability of Class III compounds is limited by barrier properties of the gastrointestinal tract. Class IV compounds are both insoluble and poorly permeable. Cyclodextrins may be particularly amenable for use with compounds that are poorly soluble. In some embodiments, the bioactive agent is a Class II or a Class IV compound under the Biopharmaceutical Classification System.

Bioactive agents may fall into one or more functional categories of therapeutic agents. For example, anti-inflammatory drugs (including non-steroidal anti-inflammatory drugs, NSAIDs) (such as celecoxib, carprofen, dexamethasone, diclofenac, flurbiprofen, hydrocortisone, indomethacin, naproxen, ketoprofen, meloxicam, nimesulide, piroxicam, prednisolone, rofecoxib, tiaprofenic acid, valdecoxib, etc.), anti-cancer drugs (such as camptothecin, imatinib, mitomycin, saponin, etc.), antibiotics (such as ampicillin, cetofiam, chloramphenicol, ciprofloxacin, cephalosporin, mitomycin, saponin, triclosan, etc.), anti-coagulants, anesthetics (such as benzocaine, bupivacaine, fentanyl, propofol, alfaxalone, etc.), and anti-glaucoma drugs (such as pilocarpine) may be incorporated into and released from the films. Some bioactive agents may fall into more than one functional category, or may not be readily cateogrized into the above-mentioned categories. Other bioactive agents that may be incorporated into and released from the films include 3-hydroxy-flavones, 17β-estradiol, acitretin, alprostadil, aripiprazole, artemisinin, bisabolol, benexate HCl, cetirzine, chlordiazepoxide, cisapride, disoxaril, dextromethrophan, diphenhydramin, chlortheophyllin, furosemide, furnidine, hesperetin, iodine, insulin, itraconazole, ketoconazole, maropitant, naftifine, natamycin, nelfinavir, nicotine, nitroglycerin, omeprazole, ozonide anti-malarials, progesterone, prostaglandins and prostaglandin derivatives (such as OP-1206, $PGE_1$, $PGE_2$, etc.), quercetin, retinoic acid, risperidone, sidenafil, teboroxime, triamterene, valsartin, voriconazole, ziprasidone mesylate, etc.

Bioactive agents with uses in non-drug applications, such as applications in the food industry, cosmetic industry, and others, may be also be incorporated into and released from films. For example, it may be desirable to release food flavoring agents, small molecules used in cosmetics, odorant molecules, and/or pheromones in a controlled manner. Films incorporating such molecules may be useful in food, cosmetics, and in household items, for example, in air fresheners, pheromone-based moth traps, etc. Bisabolol, for example, is a small molecule with anti-irritant, anti-inflammatory, anti-bacterial, and anti-fungal properties that is used in cosmetic products.

More than one bioactive agent can be released from a single film. For example, films may be constructed so as to have multiple layers of bioactive agents (each layer not necessarily containing the same bioactive agent as another layer), and/or such that the layer in each multilayer unit that comprises bioactive agents comprises more than one bioactive agent. This may be useful in applications, for example, that require or would benefit from release of more than one bioactive agent.

Associations

Inventive films generally comprise polymeric cyclodextrins that are associated with the bioactive agents that are intended to be released. Associations between the cyclodextrins and the bioactive agents can be formed before film construction. Cyclodextrins and bioactive agents are then deposited together onto a layer of an LbL film.

In some embodiments, cyclodextrins form a complex with the bioactive agent. Associations between cyclodextrins and bioactive agents are typically loose, and bonding between them is weaker than in a covalent bond. Typically, no covalent bonds are formed or broken during the formation of cyclodextrin-bioactive agent complex.

The complex may be an inclusion complex, with the cyclodextrin molecule acting as the "host" molecule. The bioactive agent may be a small molecule that fits entirely in the cavity of the cyclodextrin molecule. In some embodiments, the bioactive agent does not fit entirely inside the cavity of the cyclodextrin, but a portion of the bioactive agent molecule is located in the cavity so that the bioactive agent and the cyclodextrin molecule still form a complex. For example, it is believed that the piperidine ring of ciprofloxacin, not the whole molecule, is contained in the beta-cyclodextrin. Therefore, in some embodiments, the bioactive agent has a largest dimension less than the cavity sizes of different cyclodextrins, which are, for example, about 0.9 nm, about 0.7 nm, or about 0.6 nm. In some embodiments, a portion of the bioactive agent has a largest dimension less than about 0.9 nm, about 0.7 nm, or about 0.6 nm.

It is also possible for cyclodextrins to form non-inclusion complexes with the bioactive agent. For example, the hydroxyl groups on the outer surface of the cyclodextrin molecule may form hydrogen bonds with the bioactive agent of interest. For example, α-cyclodextrins have been shown to form both inclusion and non-inclusion complexes with dicarboxylic acids; the two types of complexes have been observed to co-exist in solution. Similarly, a 2:1 complex comprised of 2 acridine and one dimethyl-β-cyclodextrin can form when a 1:1 acrideine:dimethyl-β-cyclodextrin inclusion complex forms a non-inclusion complex with a second acridine molecule.

Polyions

Polyionic layers may be used in film construction and placed between polymeric cyclodextrin layers and polyelectrolyte layers having the same charge. For example, in some embodiments, films comprise tetralayer units having the structure (degradable cationic polyelectrolyte/polyanion/cationic polymeric cyclodextrin/polyanion). (Structures with reversed charge schemes, e.g., comprising anionic polyelectrolytes, polycations, and anionic cyclodextrins, may also be possible.)

Polyions used herein are generally biologically derived, though they need not be. Polyions that may be used include charged polysaccharides. This include glycosaminoglycans such as heparin, chondroitin, dermatan, hyaluronic acid, etc. (Some of these terms for glycoasminoglycans are often used interchangeably with the name of the sulfate form, e.g., heparan sulfate, chondroitin sulfate, etc. It is intended that such sulfate forms are included among the list of polyions. Similarly, other derivatives or forms of such polysaccharides may be incorporated into films.)

In some embodiments, polyions also add characteristics to the film that are useful for medical applications.

Dose and Release Characteristics

Certain characteristics of degradable thin films may be modulated to achieve desired doses of bioactive agents and/or release kinetics. Doses may be modulated, for example, by changing the number of multilayer units that make up the film, the type of degradable polyelectrolyte used, the type of polyion (if any) used, and/or concentrations of solutions of bioactive agents used during construction of the films. Similarly, release kinetics (both rate of release and duration of release of bioactive agent) may be modulated by changing any or a combination of the aforementioned factors.

Methods

Also provided in the disclosure are methods of releasing a bioactive agent from a thin film. Such methods generally comprise steps of providing a decomposable thin film and placing the thin film in a medium in which at least a portion of the thin film decomposes via the substantially sequential removal of at least a portion of the layers having the first charge and degradation of layers having the second charge. The medium can be, for example, provided from in vivo environment such as a subject's body. In some embodiments, the medium can be provided in an artificial environment such as tissue engineering scaffold. Buffers such as phosphate-buffered saline may also serve as a suitable medium.

Release of bioactive agents may follow linear kinetics over a period of time. Such a release profile may be desirable to effect a particular dosing regimen. Certain embodiments provide systems for releasing bioactive agents over a period of at least 2, 5, 10, or 12 days (see, for example, FIG. 18). During all or a part of the time period of release, release may follow approximately linear kinetics.

EXAMPLES

Example 1

Construction of Layer-by-Layer Films with Using a Variety of Poly(β-Amino Ester)s Characteristics of layer-by-layer (LbL) films (such as release kinetics of bioactive agents) vary depending on the type of material used to construct the films. In this Example, a variety poly (β-amino ester)s were synthesized using different monomers. Such poly (β-amino ester)s were then used to construct films by LbL deposition onto glass substrates with alternating layers of polyanions and polycations.

Materials and Methods

Reagents

All monomers were purchased from Dajac Laboratories, Inc. (Feasterville, Pa.), except 1,4 butanediol diacrylate, 1,6 hexanediol diacrylate, and 4,4-trimethylenedipiperidine, which were obtained from Alfa Aesar (Ward Hill, Mass.). Poly (sodium 4-styrene sulfonate) (SPS, $M_n$=70,000) and dextran sulfate ($M_n$=8,000) were purchased from Sigma Aldrich (St. Louis, Mo.). Dulbecco's PBS buffer and glass substrates were obtained from VWR Scientific (Edison N.J.). Linear polyethyleneimine (LPEI, $M_n$=25,000) was purchased from Polysciences, Inc (Warrington, Pa.) and $^{14}$C-dextran sulfate sodium salt (100 µCi, 1.5 mCi/g, Mn=8000) was purchased from American Radiolabeled Chemicals, Inc.

Synthesis of Poly(β-amino esters)

Poly(β-amino esters) were synthesized as previously described (Lynn et al. 2000. *Journal of the American Chemical Society*. 122: 10761-10768.). An overview of the synthetic scheme is presented in FIG. 3, along with structures of diacrylate monomers used in syntheses. In a typical experiment, a solution of 4,4-trimethylenedipiperidine (34.1 mmol) in anhydrous THF (50 mL) was added to the diacrylate monomer (34.1 mmol) dissolved in anhydrous THF (50 mL). The reaction mixture was stirred for 48 hours at 50° C. under nitrogen. After 48 hours, the reaction was cooled to room temperature and precipitated in cold stirring hexanes. Polymers were collected and dried under vacuum prior to NMR (nuclear magnetic resonance) and GPC (gel permeation chromatography) analysis. Molecular weights of polymers synthesized from each type of monomer are presented in FIG. 3.

Film Fabrication

LbL films were constructed on 1.5 $cm^2$ glass substrates using a Carl Zeiss HSM series programmable slide stainer. The glass substrates were plasma etched in oxygen using a Harrick PDC-32G plasma cleaner on high RF power for 5 minutes to generate a uniform, negatively charged surface prior to deposition. After loading onto the robotic arm, the glass substrate was dipped into a 2 mM aqueous polycation solutions for 10 minutes and then washed with agitation for 10, 20, and 30 seconds in three different water baths to remove all physically absorbed polymer. This process was repeated with the 2 mM polyanion solution to form a bilayer. All degradable polymer films were constructed on ten bilayers of linear polyethylenimine and poly (styrene sulfonate) to ensure uniform adhesion of degradable layers to the surface. These films were constructed from a pH 4.2 solution of LPEI and pH 4.7 solution of SPS. Degradable films were prepared with 10 mM polymer solutions in 100 mM acetate buffer at pH 5.0 to avoid the conditions at which poly (β-amino ester)s degrade rapidly. Following deposition, films were dried thoroughly under a stream of dry nitrogen.

Release Studies

Release profiles were investigated by monitoring the release of $^{14}$C-dextran sulfate and the degradation of non-radiolabeled films. For drug release experiments, 20 bilayer radiolabeled films were constructed using $^{14}$C-dextran sulfate solution. The radiolabled deposition solutions were prepared by combining $^{14}$C-dextran sulfate (1.5 mCi/g, $M_n$=8,000), unlabeled dextran sulfate ($M_n$=8,000), and 100 mM acetate buffer to yield a total concentration of dextran sulfate (unlabeled plus labeled) to 2 mg/mL (1 µCi/mL $^{14}$C). After fabrication, each twenty bilayer film was immersed in 30 mL phosphate buffer solution (pH 7.4, 137 mM NaCl, 2.7 mM KCl, 10 mM $Na_2HPO_4$). A 1 mL sample was extracted at various time points and analyzed via scintillation counting.

Scintillation counting was performed on a Tri-carb liquid scintillation counter (Model U2200) and the amount of radiolabel in each sample vial was measured using $^{14}C$ protocol. Degradation vials were tightly capped between sample extractions to prevent evaporation of the buffer solution. Raw data (disintegrations per minute, DPM) were converted to micrograms (μg) of drug released using the conversion factor $2.2 \times 10^6$ DPM=1 μCi, the specific radioactivity of the drug, and knowledge of the ratio of total drug to labeled drug in the deposition solution.

Film Stability Studies

Stability studies were performed with 20 bilayer films. Films were immersed in 20 mL phosphate buffer solution (PBS) in a screw top glass vial and tightly sealed. At various times, films were removed, dried thoroughly under a stream of dry nitrogen, and thickness was measured using profilometry at five predetermined locations on the film surface. Profilometry measurements were performed on a Tencor 21—profilometer. Films that could not be analyzed via profilometry were measured using ellipsometry. Ellipsometric measurements for film thickness were conducted using a Gaertner Variable Angle Ellipsometer (6328 nm, 70° incident angle) and Gaertner Variable Angle Ellipsometer Measurement Program (GEMP) Version 1.2 software interface. Following measurements, films were reimmersed in buffer solutions and resealed. All release and degradation studies were performed in triplicate.

Calculation of Octanol:Water Coefficients

Octanol: water coefficients used in this work were an average of well known computational models based on group contribution approaches (Klopman et al. 2005. *Mini-Reviews in Medicinal Chemistry.* 5: 127-133 and Tetko et al. 2005. *Comput.-Aided Mol. Des.* 19: 453-463). In general, these methods break compounds into atoms/fragments that are associated with a given constant determined from a database of structures. Correction factors are used to account for atom/fragment interactions. These estimated values are summed to produce the octanol:water coefficient in logarithmitic form (LogP). The eight methods utilized differ in both database and computational constants used, which lead to differences in logP values (Livingstone et al. 2003. *J. Curr. Top. Med. Chem.* 3: 1171-92.). Since no superior method could be selected, the average was calculated to provide a "consensus" value. This has been shown to lead to better stability of prediction (Tetko et al. 2005 and VCCLAB, Virtual Computational Chemistry Laboratory 2005; www.vcclab.org). Advanced Chemical Development, Inc., ALOGPS 2.1, and Actelion open access software were used to calculate LogP. The following computational models were used in LogP determination: ALOGPS, IALogP, AB/LogP, miLogP, KOWWIN, XLogP, ACD/LogP, and CLogP (VCCLAB).

Results

Poly (β-amino ester)s were synthesized using a variety of monomers according to the reaction scheme depicted in FIG. 3. Monomers were grouped into series in which monomers varied in alkyl chain length (AB1, A2, A3, and A4), bulk size (AB1, B2, B3), and hydrophobicity (C1, C2, C3). (See FIG. 3 for structures.) Molecular weights of poly (β-amino esters) ranged from 6,000-20,000 g/mol.

Figure 4:
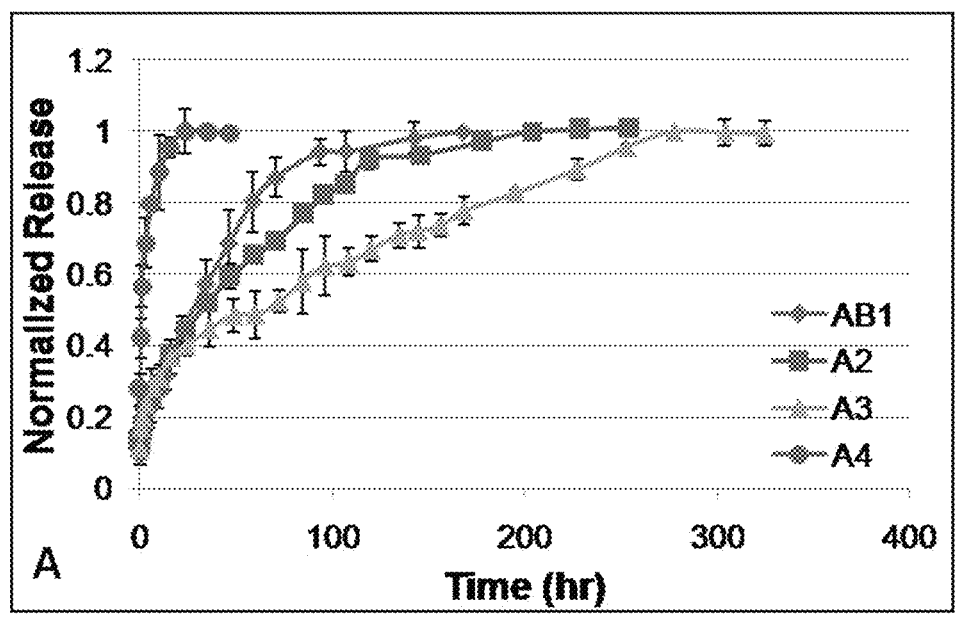
FIGS. 4A and 4B illustrate the effect of alkyl chain length on dextran sulfate release from LbL films and film stability. A series of poly (β-amino ester)s were synthesized from "A" series monomers, and the poly (β-amino ester)s were used to construct LbL films.
Figure 4:
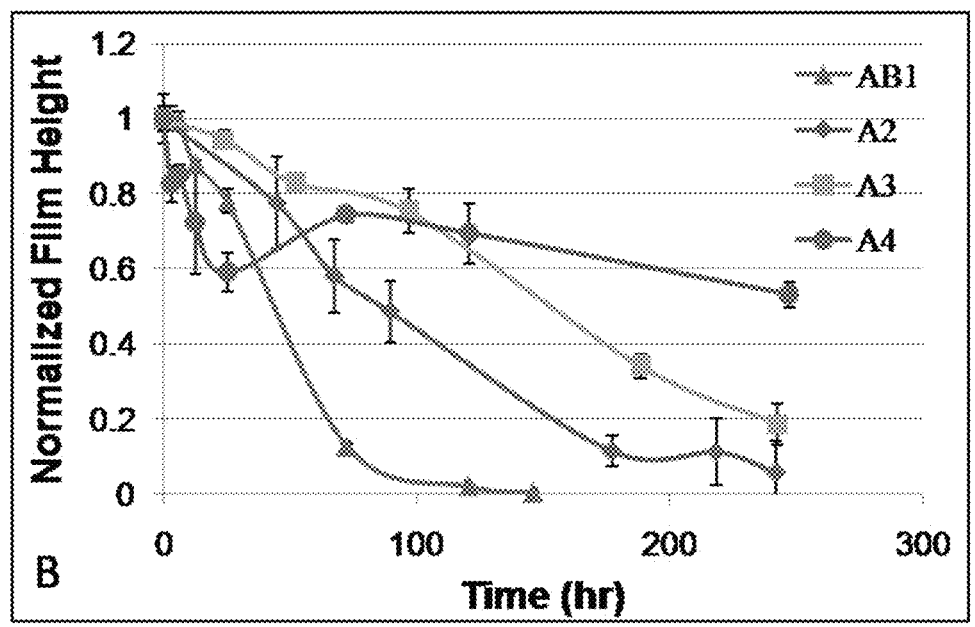
Figure 5:
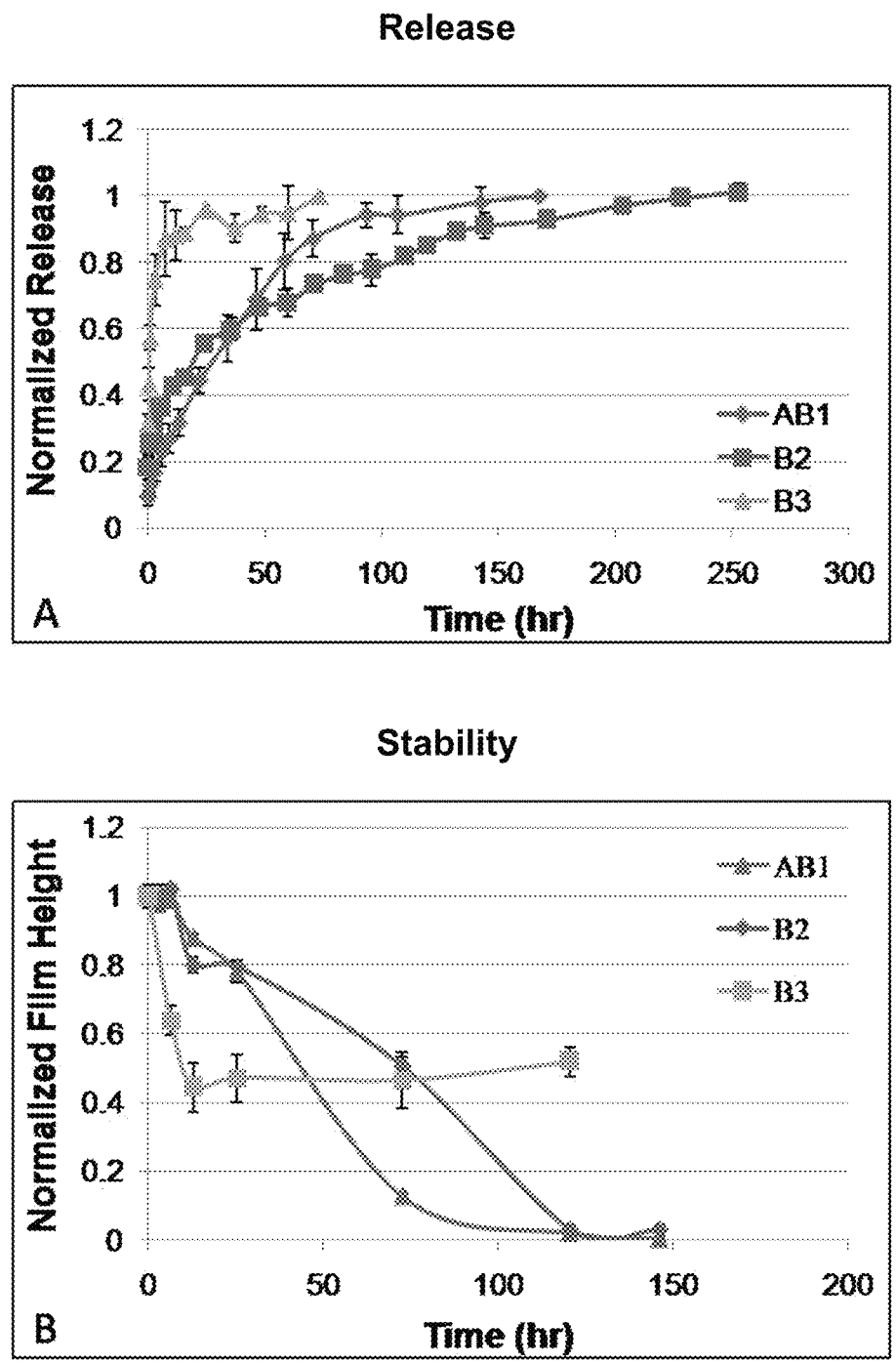
FIGS. 5A and 5B illustrate the effect of bulk size on dextran sulfate release from LbL films and film stability. A series of poly (β-amino ester)s were synthesized from "B" series monomers, and the poly (β-amino ester)s were used to construct LbL films.
Figure 6:
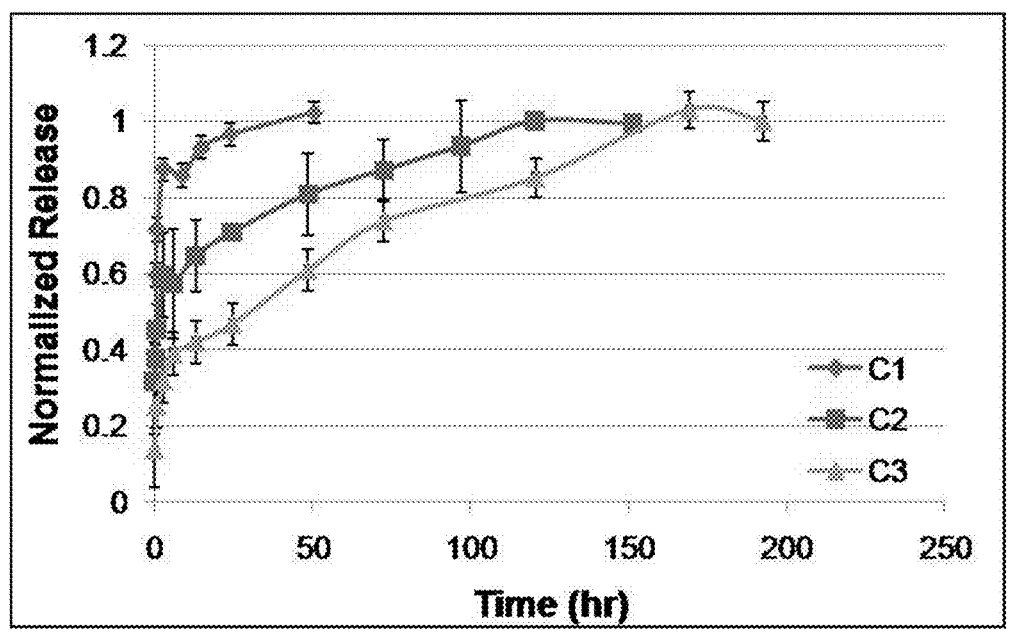
FIG. 6 illustrates the effect of hydrophobicity on dextran sulfate release from LbL films and film stability. A series of poly (β-amino ester)s were synthesized from "C" series monomers, and the poly (β-amino ester)s were used to construct LbL films. Normalized amounts of release is plotted at various timepoints.
Figure 7:
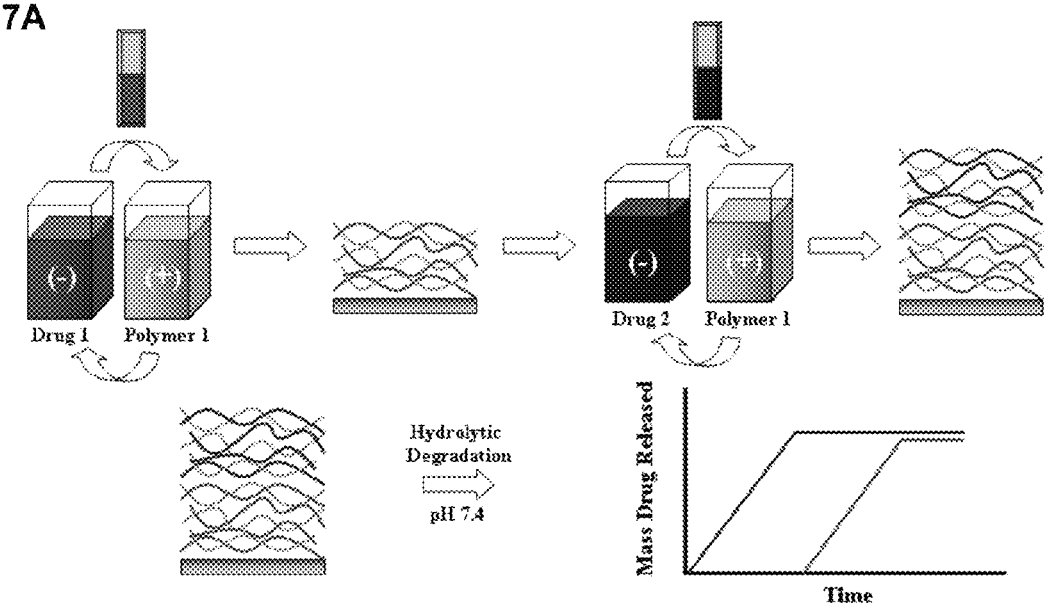
FIG. 7A and FIG. 7B illustrate methodology for LBL films.
Figure 7:
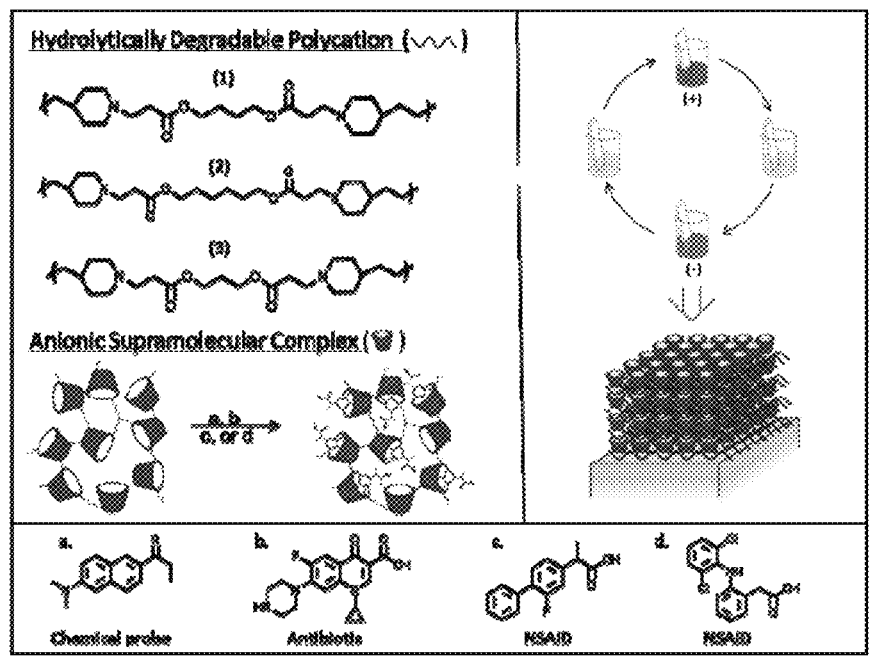
Figure 8:
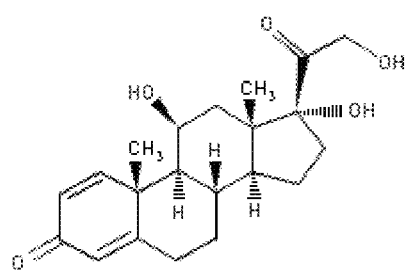
FIG. 8 depicts chemical structures of a sample of drugs with which cyclodextrin forms stable complexes. Prednisolone is an anti-inflammatory drug. Pilocarpine is an anti-glaucoma agent. Propofol is used as an anesthetic.
Figure 8:
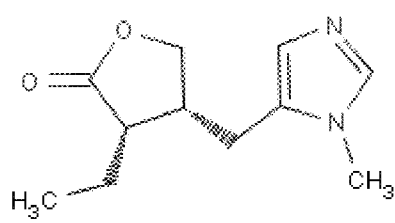
Figure 8:
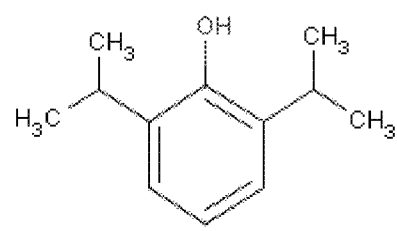

Films comprising 20 bilayers of alternating layers of poly (β-amino ester)s (the polycationic layer) and $^{14}C$-dextran sulfate incorporated into a polyanionic layer were constructed. Release and stability studies were conducted to examine the effects of alkyl chain length, bulk size, and hydrophobicity. As shown in FIG. 4A, among the alkyl chain series, poly A3 (a polymer synthesized using A3 monomers) had particularly attractive release kinetics. For films built with poly A3, dextran sulfate continued to be released for at least 8 days, with approximately linear kinetics during most of the time span analyzed. FIG. 4B presents results from stability studies on alkyl chain series polymers. Poly A3 exhibited a degradation profile that was consisted with controlled, sequential degradation of polymer layers. FIGS. 5A and 5B present results from release and stability studies on bulk size series polymers and FIG. 6 presents results from release studies on hydrophobicty series polymers. This Example provides a variety of LbL films built from different monomers, each of which have different release and stability profiles.

In addition, films constructed of different poly(β-amino esters) and the same polymeric cyclodextrins were constructed. It is believed that the substantial difference between their release duration is due to difference in the compositions of the poly(β-amino esters), and is consistent with a surface erosion mechanism based on hydrolytic degradation of the PBAE. The ability to finely control release of a small molecule with a linear profile in a sustained fashion can be very desirable for ultrathin films.

Example 2

Construction and Characterization of Layer-by-Layer Films with Cyclodextrin Inclusion Complexes In this Example, a cyclodextrin was used as carrier to incorporate drug into LbL films. Sulfobutylether β-cyclodextrin (SBE7CD) is also known as Captisol and contains 7 $SO_3^{-}$ groups per cyclodextrin molecule. Captisol was used as a carrier for dexamethasone, a corticosteroid that is used as an anti-inflammatory agent and immunosuppressant. LbL films were constructed with bilayers comprised of alternating layers of Poly 1 (see structure in FIG. 2) and Captisol-dexamethasone complexes, and release kinetics and stability of poly 1/Captisol-dexamethasone films were studied.

Materials and Methods

Reagents and solutions were obtained and prepared as described in Example 1. Captisol-dexamethasone inclusion complexes were prepared by dissolving dexamethasone in a solution of Captisol. Films comprising bilayers of poly 1/Captisol-dexamethasone were constructed by methods described in Example 1.

Release Studies

Poly 1/Captisol-dexamethasone films were placed in 10 mL of PBS. One mL samples were removed at various time points, and dexamethasone content was measured using fluorimetry. Samples were replaced after each measurement. A fluorimeter was used to obtain emission spectra of each sample, and the concentrations of dexamethasone were determined using a calibration curve. All release studies were performed in triplicate.

Film Stability Studies

Films were immersed in 20 mL phosphate buffer solution (PBS) in a screw top glass vial and tightly sealed. At various times, films were removed, dried thoroughly under a stream of dry nitrogen, and thickness was measured using ellipsometry at five predetermined locations on the film surface. Ellipsometric measurements for film thickness were conducted using a Gaertner Variable Angle Ellipsometer (6328 nm, 70° incident angle) and Gartner Ellipsometer Measurement Program (GEMP) Version 1.2 software interface. Following measurements, films were reimmersed in buffer solutions and resealed. All degradation studies were performed in triplicate.

Results

Figure 9:
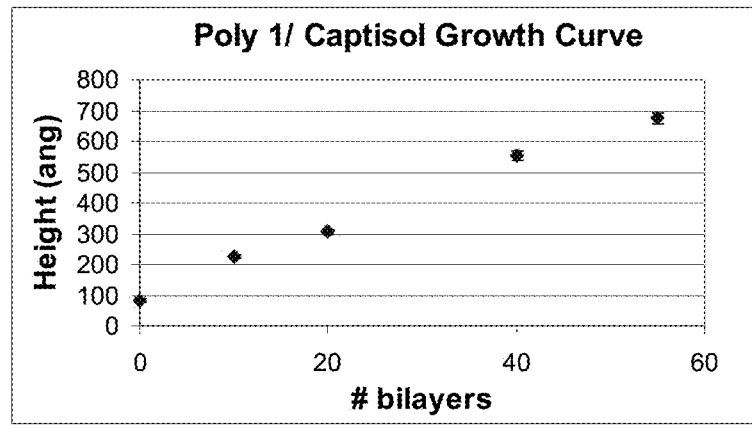
FIGS. 9A-C depict growth and release characteristics of layer-by-layer films with Captisol-Dexamethasone. Growth of Poly 1/Captisol films are shown in FIG. 9A, which shows a graph of film height plotted against number of Poly 1/Captisol bilayers.
Figure 9:
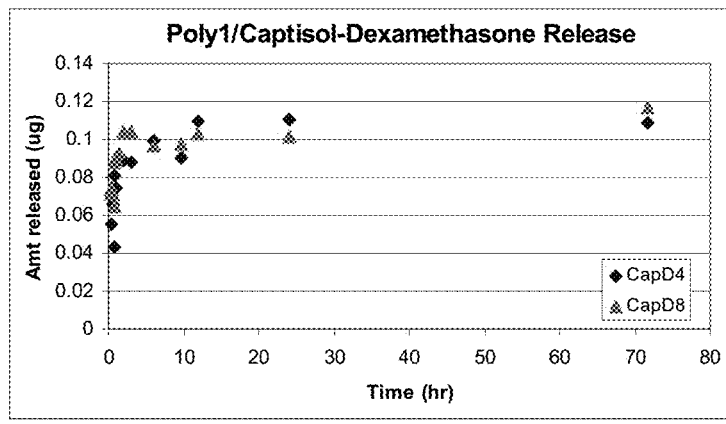
Figure 9:
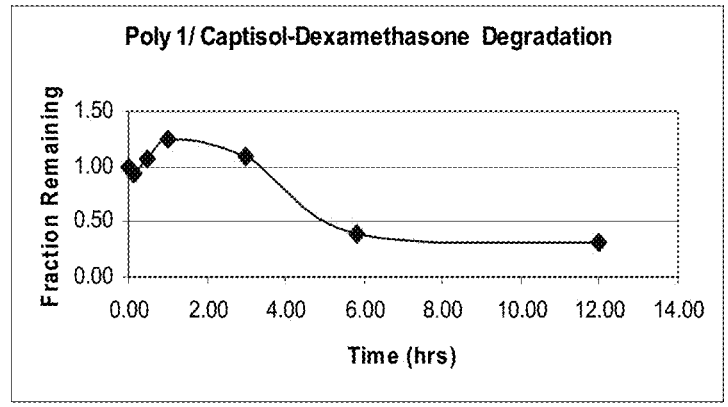

Growth characteristics of poly 1/Captisol-dexamethasone films are shown in FIG. 9A and indicate that film thickness increases roughly linearly with increased numbers of bilayers.

To examine release characteristics from poly 1/Captisol-dexamethasone films, dexamethasone was released into solution and measured at various timepoints. As shown in FIG. 9B, release from poly 1/Captisol-dexamethasone was nearly instantaneous. Nearly all of the dexamethasone that was ultimately released in the experiment was released within the first few minutes in solution.

To investigate stability of films, degradation studies of poly 1/Captisol-dexamethasone films were performed. Shown in FIG. 9C is the fraction of the film remaining (as measured by film thickness) for plottted versus time. Films swelled during the first hour in solution (as expected), but thickness decreased rapidly after the initial period of swelling. By 6 hours in solution, film thickness decreased at least 50%. These results indicate that poly 1/Captisol-dexamethasone films are highly unstable.

FIG. 10 depicts a possible mechanism for release from poly 1/Captisol-dexamethasone films. The results suggest that release of dexamethasone is not due to sequential degradation of polymer layers, but rather to film instability. Moreover, the release time scale is too short to be consistent with a top-down degradation mechanism.

Example 3

Construction and Characterization of Layer-by-Layer Films Comprising Polymeric Cyclodextrin Because LbL films built with Captisol were unstable and did not exhibit controlled release of drug, the inventors experimented with using another form of cyclodextrin. In the present Example, LbL films were built with polymeric cyclodextrin and characterized. Carboxymethyl-β-cyclodextrin (BCD) is a cyclodextrin that substituted with two COO⁻ groups per cyclodextrin molecule. BCD can be polymerized to form a polymer having a cyclodextrin backbone. Layers of polymeric BCD were deposited alternately with layers of poly 1 to form poly 1/poly(BCD) films having 20 bilayer units ((poly 1/poly(BCD))$_{20}$).

Figure 11:
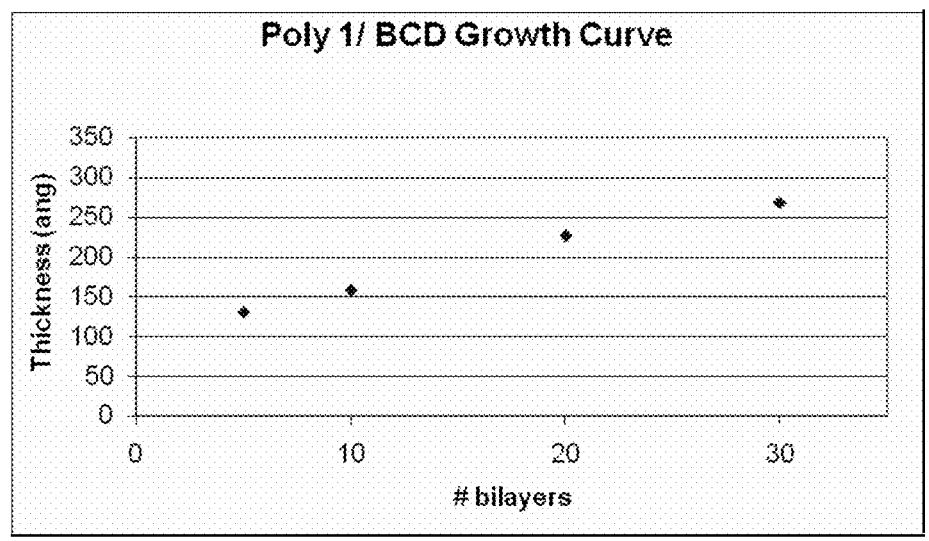
FIG. 11A depicts growth of poly 1/poly(BCD) films. Film thickness is plotted against number of poly 1/poly (BCD) bilayers.
FIG. 11B depicts stability of poly 1/poly(BCD) films put into PBS solution at pH 7.4 at 25° C. Fraction of film remaining (by thickness) is plotted versus time.
Figure 11:
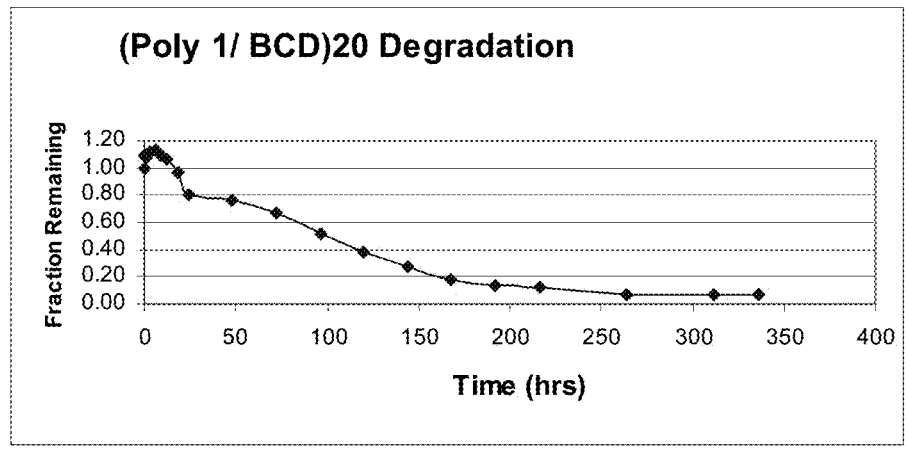

Film construction, release studies, and degradation studies were performed by methods described in Example 1, except that film construction was performed in a pH 6 environment. Films were kept in PBS pH 7.4 at 25° C. for degradation studies. As shown in FIG. 11A, thickness of poly 1/BCD films grew in an approximately linear manner with respect to number of bilayers in the film. Thickness of each individual bilayer was greater than 7.9 nm, the minimum thickness possible for a bilayer containing cyclodextrins.

Stability studies were performed on poly 1/poly(BCD) films. As shown in FIG. 11B, poly 1/poly(BCD) films exhibited a controlled degradation after an initial brief period of swelling in solution. Degradation occurred gradually over a course of several days, as opposed to the rapid degradation seen with poly 1/Captisol-dexamethasone films. These results indicate that LbL films comprising polymeric cyclodextrin are relatively stable.

Example 4

Release of Antibiotic from Polymeric Cyclodextrin-Containing LbL Films

To test the release of drug from polymeric cyclodextrin-containing LbL films, polymeric cyclodextrin-drug inclusion complexes were made and then used to construct LbL films. In this example, poly 1/poly(BCD)-ciprofloxacin films were constructed and release of ciprofloxacin was studied. Ciprofloxacin is highly sensitive aromatic molecule that is used as broad spectrum antibiotic. Ciprofloxacin fluoresces and is uncharged at a neutral pH. (See structure shown in FIG. 12A.)

Materials and Methods

Film construction was performed by methods described in Example 1.

Formation of Inclusion Complexes

Poly(carboxymethyl β-cyclodextrin) (poly(BCD)) solutions were made by dissolving poly(BCD) in 0.1 M sodium acetate buffer at pH 6 to a final concentration of 20 mg/mL (2.5 μM). Poly (BCD)-ciprofloxacin inclusion complexes were formed by dissolving ciprofloxacin in 2.5 μM poly (BCD).

Release Studies

Release profiles were investigated by monitoring the release of the small molecule using a fluorimeter and the degradation of non-radiolabeled films. For drug release experiments, 20 bilayer films were constructed using carboxymethylbeta-cyclodextrin polymer:drug conjugate solution. The deposition solutions were prepared by combining 25 μM carboxymethylbeta-cyclodextrin polymers solution in 0.1 M sodium acetate buffer (1 $M_n$=8,000), with the various small molecules. After fabrication, each twenty bilayer film was immersed in 10 mL phosphate buffer solution (pH 7.4, 137 mM NaCl, 2.7 mM KCl, 10 mM $Na_2HPO_4$). A 1 mL sample was extracted at various time points and analyzed via fluorescence spectroscopy. Degradation vials were tightly capped between sample extractions to prevent evaporation of the buffer solution. Raw spectrum data were converted to micrograms (μg) of drug released using a calibration curve for a given molecule at a defined emission wavelength.

Results

Ciprofloxacin was successfully incorporated into LbL films as part of inclusion complexes with poly(BCD). Ciprofloxacin was released from poly 1/poly(BCD)-ciprofloxacin films and the amount of released ciprofloxacin was measured by obtaining fluorescent emission spectra of samples of release buffer at various time intervals. In this assay, increased fluorescent intensity is indicative of increased amount of ciprofloxacin.

Figure 12:
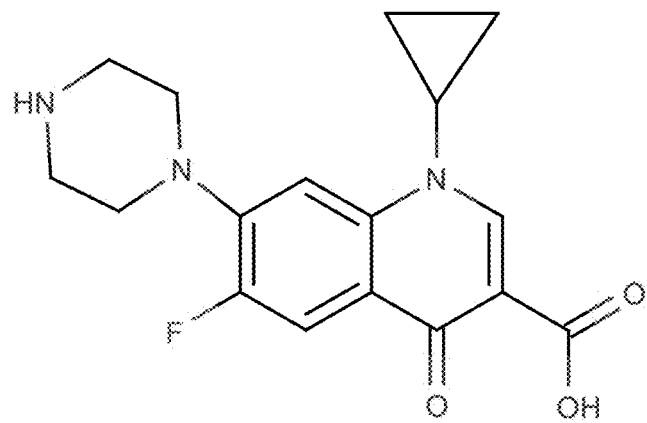
FIG. 12A depicts the chemical structure of ciprofloxacin, a broad spectrum antibiotic that fluoresces naturally due to its aromatic structure.
FIG. 12B depicts release characteristics from poly 1/poly (BCD)-ciprofloxacin films. Poly 1/poly (BCD)-ciprofloxacin films were put into phosphate-buffered saline (PBS) solution, and fluorescent intensity of the solution was scanned at various time points ranging from 0.83 hours to 69.3 hours in solution. Increased fluorescent intensity indicates increased amounts of Ciprofloxacin released into solution.
Figure 12:
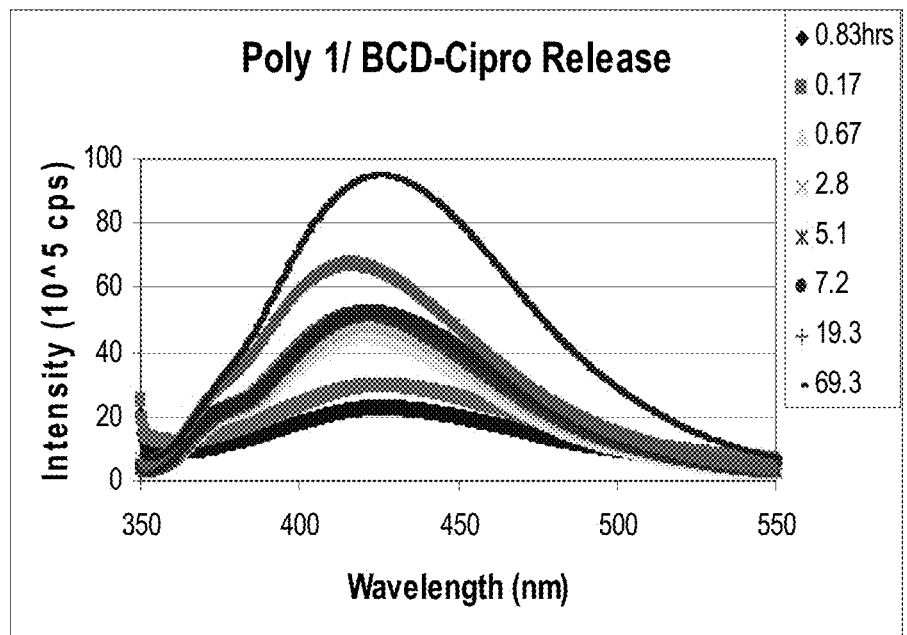

Shown in FIG. 12B are the emission spectra of release buffer samples taken at various time points after films were put in solution. Ciprofloxacin continued to be released for days, at least through the latest time point tested (69.3 hours, or approximately 2.9 days).

These results demonstrate successful incorporation of an small molecule bioactive agent (in this example, an antibiotic) into LbL films using polymeric cyclodextrins as carriers, and subsequent controlled release of the bioactive agent from the films.

Example 5

Mechanism of Release from Polymeric Cyclodextrin-Containing LbL Films

In this Example, release of a probe was studied to understand the mechanism of release from polymeric cyclodextrin-containing LbL films.

Figure 13:
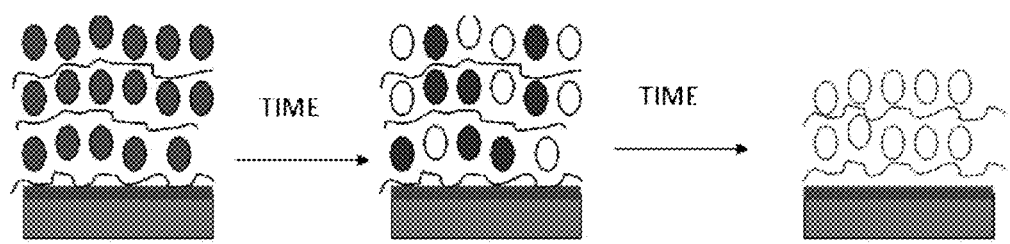
FIGS. 13A and 13B depict possible mechanisms of drug release from poly 1/poly (BCD)-drug films.
Figure 13:
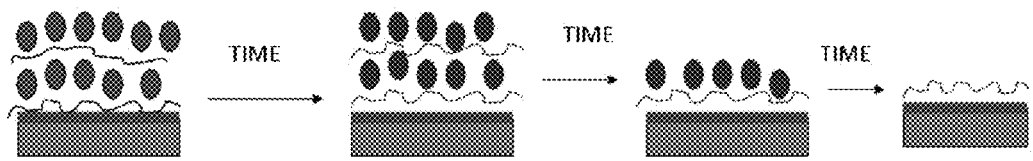

FIGS. 13A and 13B present two possible and alternative release mechanisms. In the schematic of FIG. 13A, the bioactive agent diffuses out of the film without the cyclodextrin. In the schematic of FIG. 13B, the bioactive agent is released together with and inside cyclodextrin.

Figure 14:
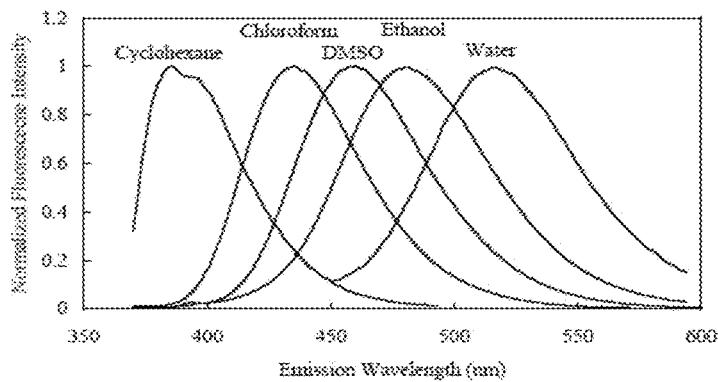
FIGS. 14A-C are directed to addressing the mechanism of release from (poly 1/poly(BCD)) films. Prodan, a fluorescent dye that is sensitive to the polarity of its environment, was complexed with BCD and incorporated into poly 1-containing layer-by-layer films.
Figure 14:
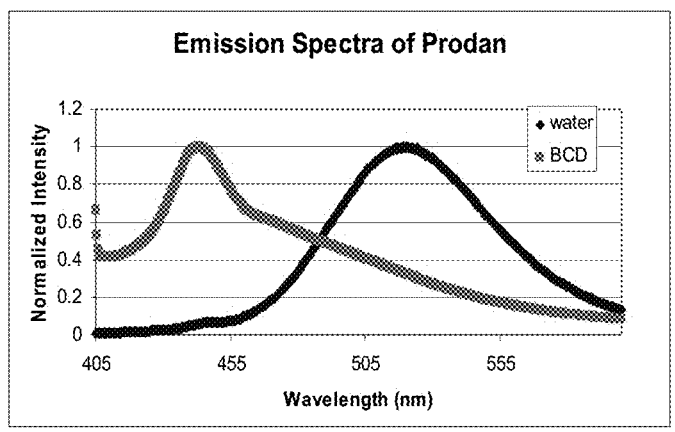
Figure 14:
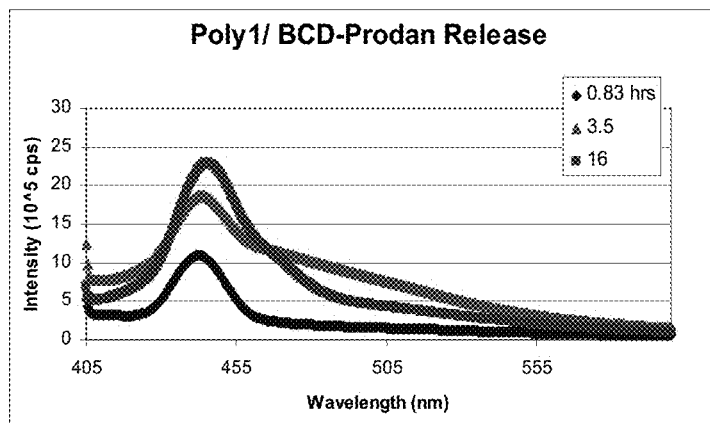

The experiments described in this example made use of prodan (6-propionyl-2-dimethylaminonaphthalene), a solvachromatic fluorescent probe. Fluorescence of prodan is sensitive to the polarity of its environment. When prodan is surrounded by a polar environment, it fluoresces in a relaxed state, producing a large shift in the emission spectrum. When prodan is surrounded by a nonpolar environment, it fluoresces in an unrelaxed state, resulting in a small shift. FIG. 14A shows the emission spectra of prodan in a variety of solvents. Shown in FIG. 14B are the emission spectra of prodan in water and in BCD.

Poly(BCD)-prodan inclusion complexes were made by dissolving prodan in poly(BCD) as described for poly(BCD)-ciprofloxacin inclusion complexes in Example 3. (Poly 1/poly(BCD)-prodan)$_{20}$ films were constructed by layer-by-layer deposition and prodan release studies were conducted as described in Example 1.

Release of prodan from poly 1/poly(BCD)-prodan films was measured at various timepoints ranging from 0.83 hours to 16 hours. The emission spectra of released prodan at all timepoints tested were similar to the emission spectrum of prodan in BCD (compare FIGS. 14B and 14C), indicating that prodan was released while still inside BCD.

These results show that prodan is released while still in the cyclodextrin interior, indicating a surface erosion mechanism as depicted in FIG. 13B, that is, bioactive agents are released inside cyclodextrin.

Example 6

Release of Anti-Inflammatory Agents from Polymeric Cyclodextrin-Containing LbL Films The experiments in this Example demonstrate that a number of anti-inflammatory drug can be incorporated into LbL films using polymeric cyclodextrins as carriers and that such anti-inflammatory agents can be released in a controlled manner from such films.

Materials and Methods

Formation of poly(BCD): drug inclusion complexes and film construction were achieved by methods as described in Examples 1-3; release studies were performed as described in Example 4. Solubility values and complexation coefficients were determined and/or calculated according to previously published methods (Brewster et al. 2007. "Cyclodextrins as pharmaceutical solubilizers." *Advanced Drug Delivery*. 59: 645-666).

Results

Figure 15:
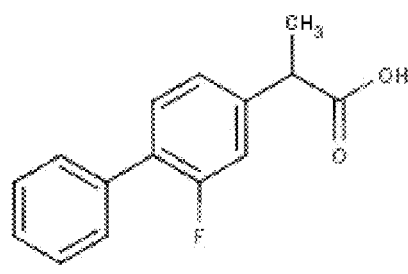
FIG. 15 depicts chemical structures of certain anti-inflammatory drugs that were complexed with polymeric cyclodextrins and incorporated into layer-by-layer films in experiments described herein.
Figure 15:
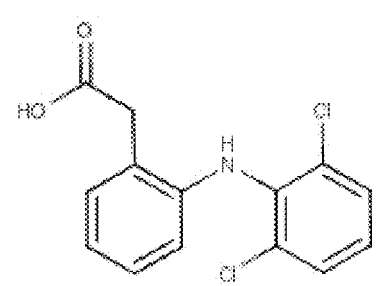
Figure 15:
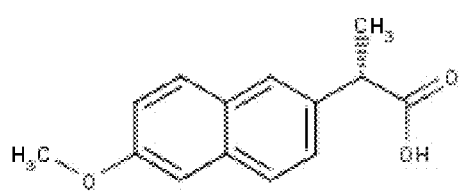
Figure 15:
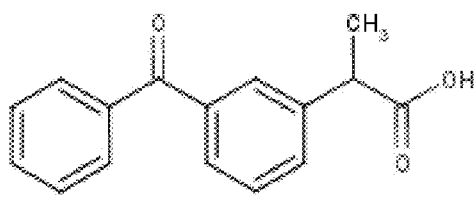

Flurbiprofen, diclofenac, naproxen, and ketoprofen are non-steroidal anti-inflammatory drugs. Shown in FIG. 15 are the chemical structures of these drugs and listed in table 2 are some known indications for each drug. The list of indications is meant to be representative and does not necessarily encompass all uses for the drugs.

TABLE 2

Indications for anti-inflammatory drugs

| Drug | Indications |
|---|---|
| Ketoprofen | Arthritis |
|  | Soft tissue injury |
|  | Ocular inflammation |
| Diclofenac | Arthritis |
|  | Pain |
|  | Acute migraines |
|  | Fever |

TABLE 2-continued

Indications for anti-inflammatory drugs

| Drug | Indications |
|---|---|
| Naproxen | Inflammation |
|  | Pain |
|  | Fever |
|  | Prostaglandin blocker |
| Flurbiprofen | Antimiotic agent |
|  | Pain |
|  | Arthritis |
|  | Ocular inflammation |

Presented in Table 3 are experimentally determined solubility values of these drugs in water ($S_0$) and complexed with cyclodextrins ($S_t$) and calculated complexation coefficients ($K_c$).

TABLE 3

Solubility and Complexation Coefficients

| Drug | $S_0$ (mg/mL) | $S_t$ (mg/mL) | $K_c$ (M$^{-1}$) |
|---|---|---|---|
| Ketoprofen | 0.051 | 2.71 | 5000 |
| Diclofenac | 0.002 | 2.8 | — |
| Naproxen | 0.016 | 0.84 | 4300 |
| Flurbiprofen | 0.008 | 0.54 | 4930 |

Figure 16:
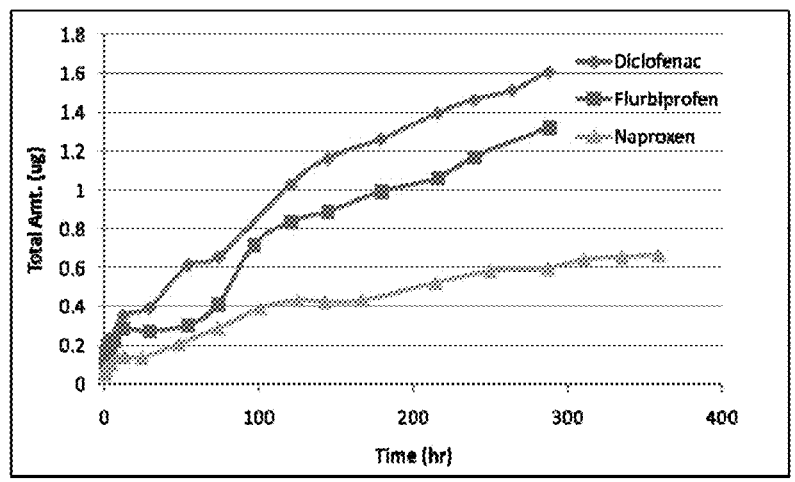
FIGS. 16A and 16B depict release of anti-inflammatory drugs (diclofenac, flurbiprofen, and naproxen) and dextran sulfate from (Poly A3/BCD-drug)$_{20}$ films.
Figure 16:
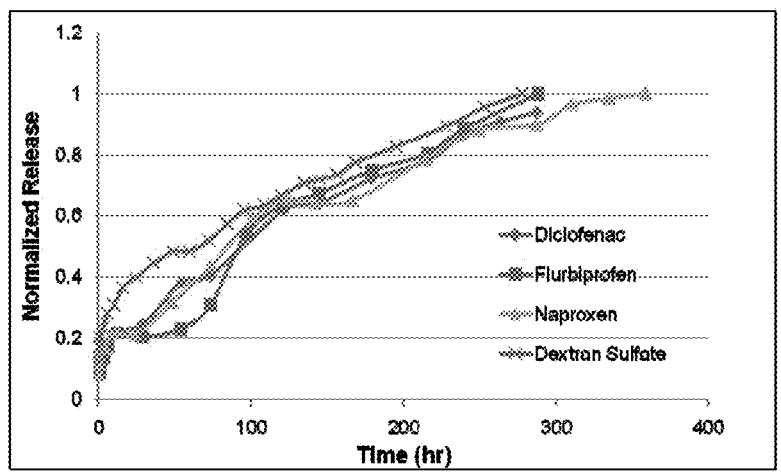

Poly A3 (see FIG. 3) was used to construct (Poly A3/poly (BCD)-drug)$_{20}$ films for each of the drugs diclofenac, flurbiprofen, and naproxen. Release of drug into solution was measured at various timepoints. Shown in FIG. 16A is a plot of total amount of drug released versus time for each drug. Drugs continued to be released over a time span of at least about 12 days for all three drugs tested in this set of experiments. Presented in Table 4 are release rates from poly A3/poly(BCD) films and $R^2$ statistical values for diclofenac, flurbiprofen, naproxen.

TABLE 4

Release rates of anti-inflammatory agents

| Therapeutic | Release Rate | R2 |
|---|---|---|
| Diclofenac | 5 ng/hr | 0.974 |
| Flurbiprofen | 4 ng/hr | 0.965 |
| Naproxen | 1 ng/hr | 0.952 |

When amounts of released drug were normalized by dividing by the total amount of drug released over the timespan of the experiments, all three drugs showed similar release profiles to each other and to dextran sulfate. (See FIG. 16B).

These results indicate that several anti-inflammatory drugs can be incorporated into films using polymeric cyclodextrin carriers and that controlled release of such drugs is observed from LbL films. Moreover, release profiles appear to be independent of the type of drug, indicating that release characteristics of one drug or compound may be informative of release characteristics for other drugs.

To determine if polymeric cyclodextrin alters drug activity, the inhibition of cyclooxygenase (COX) by diclofenac was investigated. COX is the rate limiting enzyme in the production of prostaglandins, which are important in homeostasis and inflammatory pathways (T. D. Warner et al., *Proceedings of the National Academy of Sciences of the United States of America* 1999, 96, 9966). A549 human lung carcinoma cells were exposed to aliquots of release buffer, and prostaglandin E₂ concentration was measured. In the experiment, the release buffer was replaced every 24 hours, so that time points measured the activity of the drug released during each specific 24 hour period. The measured activity does not include the additive effect of drug that may accumulate in a body cavity or localized tissue from the surface of an implant, which would be even higher than that reported. The result shows that the diclofenac is highly active over the time course of film release, leading to COX inhibition and suppressed prostaglandin production. This work thus demonstrates the release of active drug from slow-releasing ultrathin films of thickness less than a micron that are capable of delivering therapeutic levels of drug. The approach here is a utilization of a charged polymeric carrier capable of facile reversible complexation with the drug of choice in alternation with a degradable polyion. Charged cyclodextrin polymers were used for the trapping of cyclodextrin-drug complexes in stable, surface eroding films capable of drug release within the cyclodextrin carrier without altering activity. Release kinetics were found to be independent of the therapeutic incorporated and can be regulated through choice of degradable polycation. This technology can be applied to nanomedicine coatings for applications in personalized medicine, transdermal delivery, medical devices, nanoparticulate carriers, prosthetic implants, as well as small molecules for imaging, agriculture, and basic scientific research.

All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

Other Embodiments and Equivalents

While the present disclosures have been described in conjunction with various embodiments and examples, it is not intended that they be limited to such embodiments or examples. On the contrary, the disclosures encompass various alternatives, modifications, and equivalents, as will be appreciated by those of skill in the art. Accordingly, the descriptions, methods and diagrams of should not be read as limited to the described order of elements unless stated to that effect.

Although this disclosure has described and illustrated certain embodiments, it is to be understood that the disclosure is not restricted to those particular embodiments. Rather, the disclosure includes all embodiments that are functional and/or equivalents of the specific embodiments and features that have been described and illustrated.

We claim:

1. A decomposable thin film, comprising:
   at least one multilayer repeat unit, the multilayer repeat unit including at least a first polyelectrolyte layer and a second polyelectrolyte layer, the first polyelectrolyte layer having a first electrostatic charge and the second polyelectrolyte layer having a second electrostatic charge, the first and second electrostatic charges being opposite, wherein:
   the first polyelectrolyte layer comprises a polycyclodextrin; and
   the second polyelectrolyte layer comprises a degradable polyelectrolyte,
   wherein the polycyclodextrin is non-covalently associated with a bioactive agent, and
   wherein the bioactive agent is a hydrophobic molecule.

2. The decomposable thin film of claim 1, wherein:
   the degradable polyelectrolyte is hydrolytically degradable.

3. The decomposable thin film of claim 1, wherein the polycyclodextrin is a polymer comprising a cyclodextrin backbone.

4. The decomposable thin film of claim 1, wherein the polycyclodextrin includes one or more cyclodextrin moieties selected from the group consisting of an α-cyclodextrin, a β-cyclodextrin, and a γ-cyclodextrin.

5. The decomposable thin film of claim 4, wherein the one or more cyclodextrin moieties are β-cyclodextrins.

6. The decomposable thin film of claim 4, wherein the one or more cyclodextrin moieties are selected from the group consisting of a dimethyl-β-cyclodextrin (DMβCD), a trimethyl-β- cyclodextrin (TMβCD), a randomly methylated-β-cyclodextrin (RMβCD), a hydroxyethyl-β-cyclodextrin (HEβCD), a 2-hydroxypropyl-β-cyclodextrin (HPβCD), a 3-hydroxypropyl-βcyclodextrin (3HPβCD), a 2,3-dihydroxypropyl-β-cyclodextrin (DHPβCD), a 2-hydroxyisobutyl-β-cyclodextrin (HIBβCD), a sulphobutylether-β-cyclodextrin (SBEβCD), a carboxymethyl-β-cyclodextrin, a glucosyl-β-cyclodextrin ($G_1\beta CD$), and a maltosyl-β-cyclodextrin ($G_2\beta CD$).

7. The decomposable thin film of claim 6, wherein the one or more cyclodextrin moieties are carboxymethyl-β-cyclodextrins.

8. The decomposable thin film of claim 1, wherein the polycyclodextrin in non-covalent association with a hydrophobic molecule forms an inclusion complex.

9. The decomposable thin film of claim 1, wherein the polycyclodextrin includes at least one cyclodextrin moiety having a cavity diameter of less than about 0.9 nm as measured between anomeric oxygen atoms.

10. The decomposable thin film of claim 9, wherein the polycyclodextrin includes at least one cyclodextrin moiety having a cavity diameter of less than about 0.7 nm as measured between anomeric oxygen atoms.

11. The decomposable thin film of claim 10, wherein the polycyclodextrin includes at least one cyclodextrin moiety having a cavity diameter of less than about 0.6 nm as measured between anomeric oxygen atoms.

12. The decomposable thin film of claim 1, wherein the bioactive agent is a Class II or Class IV compound according to the Biopharmaceutical Classification System (BCS).

13. The decomposable thin film of claim 1, wherein the bioactive agent is selected from the group consisting of an anti-inflammatory drug, an anti-cancer drug, an antibiotic, an anti-coagulant, an anesthetic, and an anti-glaucoma drug.

14. The decomposable thin film of claim 13, wherein the bioactive agent is an anti-inflammatory drug selected from the group consisting of celecoxib, carprofen, dexamethasone, diclofenac, flurbiprofen, hydrocortisone, indomethacin, naproxen, ketoprofen, meloxicam, nimesulide, piroxicam, prednisolone, rofecoxib, tiaprofenic acid, and valdecoxib.

15. The decomposable thin film of claim 13, wherein the bioactive agent is an anti-cancer drug selected from the group consisting of camptothecin, imatinib, mitomycin, saponin, and combinations thereof.

16. The decomposable thin film of claim 13, wherein the bioactive agent is an antibiotic selected from the group consisting of ampicillin, cetofiam, chloramphenicol, ciprofloxacin, cephalosporin, mitomycin, saponin, and triclosan.

17. The decomposable thin film of claim 13, wherein the bioactive agent is an anesthetic selected from the group consisting of alfaxalone, benzocaine, bupivacaine, fentanyl, and propofol.

18. The decomposable thin film of claim 13 wherein the bioactive agent is pilocarpine.

19. The decomposable thin film of claim 1, wherein the bioactive agent is a food flavoring agent.

20. The decomposable thin film of claim 1, wherein the degradable polyelectrolyte is a polymer selected from one or more members of the group consisting of a polyester, a polyanhydride, a polyorthoester, a polyphosphazene, and a polyphosphoester.

21. The decomposable thin film of claim 20, wherein the polymer is a polyester selected from the group consisting of a poly(β-amino ester), a poly(L-lactide-co-L-lysine), a poly(serine ester), a poly(4-hydroxy-L-proline ester), and a poly[α-(4-aminobutyl)-L-glycolic acid].

22. The decomposable thin film of claim 21, wherein the polyester is a poly(β-amino ester) that includes a repeating unit represented by a structural formula selected from the group consisting of

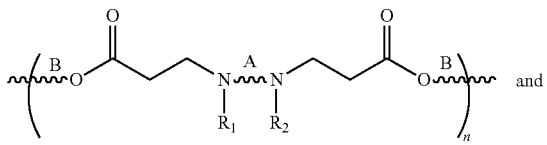

-continued

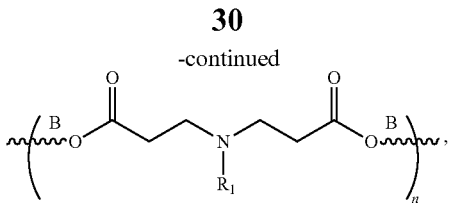

wherein linker A, linker B, R$_1$, and R$_2$ each independently is a substituted or unsubstituted, branched or unbranched chain of carbon atoms or heteroatoms.

23. The decomposable thin film of claim 22, wherein the poly(β-amino ester) includes a repeating unit represented by a structural formula selected from the group consisting of:

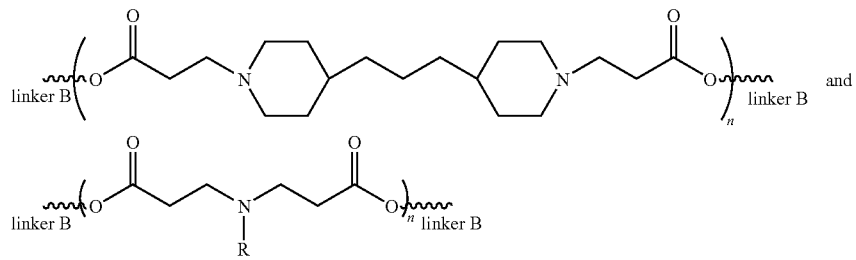

wherein:
each linker B independently is a carbon chain of 1 to 30 carbon atoms or a heteroatom-containing carbon chain of 1 to 30 atoms, each of which is optionally substituted with at least one group selected from a branched or unbranched alkyl, a branched or unbranched alkenyl, a branched or unbranched alkynyl, an amino, an alkylamino, a dialkylamino, a trialkylamino, an aryl, a ureido, a heterocyclic, an aromatic heterocyclic, a cyclic, an aromatic cyclic, a halogen, hydroxyl, an alkoxy, a cyano, an amide, a carbamoyl, a carboxylic acid, an ester, a carbonyl, a carbonyldioxyl, an alkylthioether, or a thiol group;

each R independently is hydrogen, a branched and unbranched alkyl, a branched or unbranched alkenyl, a branched or unbranched alkynyl, an aryl, a halogen, a hydroxyl, an alkoxy, a carbamoyl, a carboxyl ester, a carbonyldioxyl, an amide, a thiohydroxyl, an alkylthioether, an amino, an alkylamino, a dialkylamino, a trialkylamino, a cyano, a ureido, a substituted alkanoyl, a cyclic, a cyclic aromatic, a heterocyclic, and an aromatic heterocyclic group, each of which is further optionally substituted with at least one substituent selected from the group consisting of a branched or unbranched alkyl, a branched or unbranched alkenyl, a branched or unbranched alkynyl, an amino, an alkylamino, a dialkylamino, a trialkylamino, an aryl, a ureido, a heterocyclic, an aromatic heterocyclic, a cyclic, an aromatic cyclic, a halogen, a hydroxyl, an alkoxy, a cyano, an amide, a carbamoyl, a carboxylic acid, an ester, a carbonyl, a carbonyldioxyl, an alkylthioether, and a thiol group; and n is an integer greater than or equal to 5.

24. The decomposable thin film of claim 23, wherein the repeating unit is represented by a structural formula selected from the group consisting of:

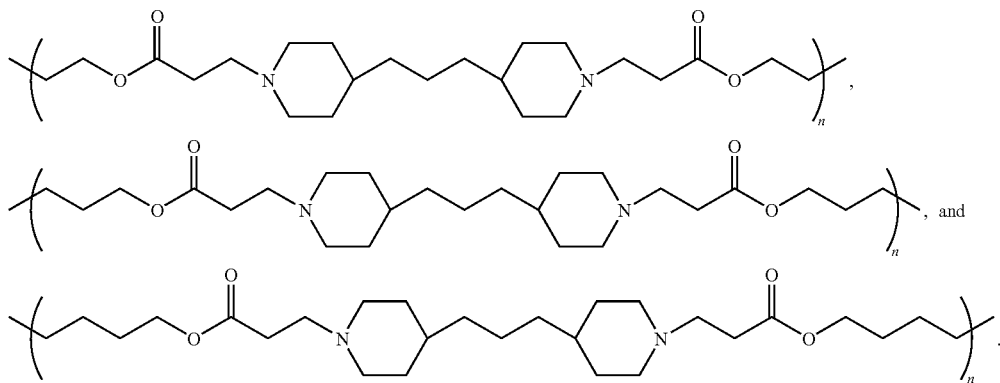

25. The decomposable thin film of claim 24, wherein the repeating unit is represented by the structural formula

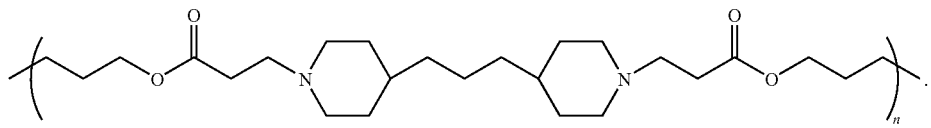

26. The decomposable thin film of claim 1, wherein at least a portion of the degradable polyelectrolyte layers comprises a polymer selected from poly(styrene sulfonate), poly(acrylic acid), linear poly(ethylene imine), poly(diallyl dimethyl ammonium chloride), poly(allylamine hydrochloride), and combinations thereof.

27. The decomposable thin film of claim 1, wherein the degradable polyelectrolyte is degradable via a process selected from the group consisting of hydrolytic degradation, thermal degradation, enzymatic degradation, and photolytic degradation.

28. The decomposable thin film of claim 1, wherein at least a portion of the degradable polyelectrolyte layers comprises a biodegradable polymer.

29. The decomposable thin film of claim 28, wherein the biodegradable polymer is selected from polyhydroxyacids; polypropylfumerates; polycaprolactones; polyamides; poly (amino acids); polyacetals; polyethers; biodegradable polycyanoacrylates; biodegradable polyurethanes; polysaccharides; and co-polymers, mixtures, and adducts thereof.

30. The decomposable thin film of claim 1, wherein the thin film is a hollow shell.

31. The decomposable thin film of claim 1, further including a substrate, optionally coated by a primer layer, in contact with the thin film.

32. The decomposable thin film of claim 1, wherein the film comprises at least 10 multilayer repeat units.

33. The decomposable thin film of claim 32, wherein the film comprises at least 20 multilayer repeat units.

34. The decomposable thin film of claim 1, wherein the multilayer repeat unit further includes a third polyelectrolyte layer.

35. The decomposable thin film of claim 34, wherein the multilayer repeat unit further includes a fourth polyelectrolyte layer comprising a degradable polyelectrolyte.

36. The decomposable thin film of claim 3, wherein the polycyclodextrin is a polymer comprising cyclodextrin as a pendant group.

* * * * *